United States Patent [19]

Kakuda et al.

[11] Patent Number: 5,736,575

[45] Date of Patent: Apr. 7, 1998

[54] EXCITEMENT ACCELERATING AGENT

[75] Inventors: Takami Kakuda; Takanobu Takihara; Iwao Sakane; Ayumu Nozawa, all of Shizuoka, Japan

[73] Assignee: Ito En Ltd., Tokyo, Japan

[21] Appl. No.: 720,198

[22] Filed: Sep. 25, 1996

[30] Foreign Application Priority Data

Oct. 3, 1995 [JP] Japan .................... 7-256615

[51] Int. Cl.$^6$ .................... A61K 31/195
[52] U.S. Cl. .................... 514/563
[58] Field of Search .................... 514/563

[56] References Cited

FOREIGN PATENT DOCUMENTS 4-253916  9/1992  Japan .

*Primary Examiner*—Kimberly Jordan
*Attorney, Agent, or Firm*—Lowe, Price, LeBlanc & Becker

[57] ABSTRACT

An excitement accelerating agent was produced by incorporating a very small amount of theanine as an effective compoment in a range that shows the excitement accelerating action. The very small amount in a range that shows the excitement accelerating action means a range containing theanine in an amount of from about 0.17 mg/kg to 0.85 mg/kg, preferably from about 0.17 mg/kg to 0.34 mg/kg based on the weight as an injection agent, and in an amount of from about 0.20 mg/kg to 2.8 mg/kg, preferably from about 0.50 mg/kg to 2.5 mg/kg (0.17/0.338–0.85/0.338) as an oral agent. A safe and effective excitement accelerating agent can be provided by utilizing sufficiently the excitement accelerating action given by theanine, and if it is regularly taken for a long period of time, it is also effective as a nutritious tonic, an energy-increasing agent, and a stamina-sustaining agent.

7 Claims, 30 Drawing Sheets

EXCITEMENT ACCELERATING AGENT

BACKGROUND OF THE INVENTION

1. Field of the Invention

The present invention relates to an excitement accerelating agent.

2. Description of the Prior Art

Theanine is a substance separated as one ingredient of green tea in 1950s, and this substance is L-glutamic acid-γ-ethylamide. This theanine has conventionally known as a flavoring ingredient of tea, and designated as one of food additives. Recently, the caffeine excitement-suppressing action of the theanine has been discovered, and an invention (Japanese Laid-Open Patent Publication No. 253916/1992) has been disclosed which utilizes this action to suppress the exciting action of caffeine while maintaining the taste and flavor of foods and drinks containing caffeine, by adding thereto theanine extracted from tea at a certain concentration or higher.

SUMMARY OF THE INVENTION

The present inventors made investigations relating to actions of theanine with respect to the brain neurons, and as a result, this invention has been completed.

Namely, theanine was dosed to animals to be tested by changing the dose and the brain waves of animals to be tested were measured after dosing. As a result, the brain waves surely show the stable mental status in a conventional general range of dose, and a result showing the excitement suppressing action of theanine could be obtained. However, when the dose of theanine is adjusted to less than a certain range, surprisingly, the brain waves show the excited state, and a result showing the excitement accelerating action of theanine could be obtained. Moreover, another test for dosing theanine to animals to be tested was conducted under other conditions in order to confirm this result, and the similar results could be obtained.

Therefore, the object of the present invention is to provide an excitement accelerating agent derived from theanine.

The present invention is characterized in an excitement accelerating agent containing a small amount of theanine as an effective component in a range of showing the excitement accelerating action.

This excitement accelerating agent is characterized in that the excitement accelerating action appears by adjusting the dose of theanine to a very small amount. This is demonstrated by Experiment 1 and Experiment 2 using rats described later.

According to the present invention, by utilizing the excitement accelerating action given by theanine efficiently, a safe and effective excitement accelerating agent can be provided. Furthermore, if the excitement accelerating agent of the present invention is used regularly for a long period of time, it is effective also as a nutritious tonic, an energy-increasing agent, and a stamina-sustaining agent. Moreover, by the energy-increasing action and the stamina-sustaining action of the excitement accelerating agent, it can be considered to be effective for prevention of growing fat and aging.

DETAILED DESCRIPTION OF THE INVENTION

Figure 1:
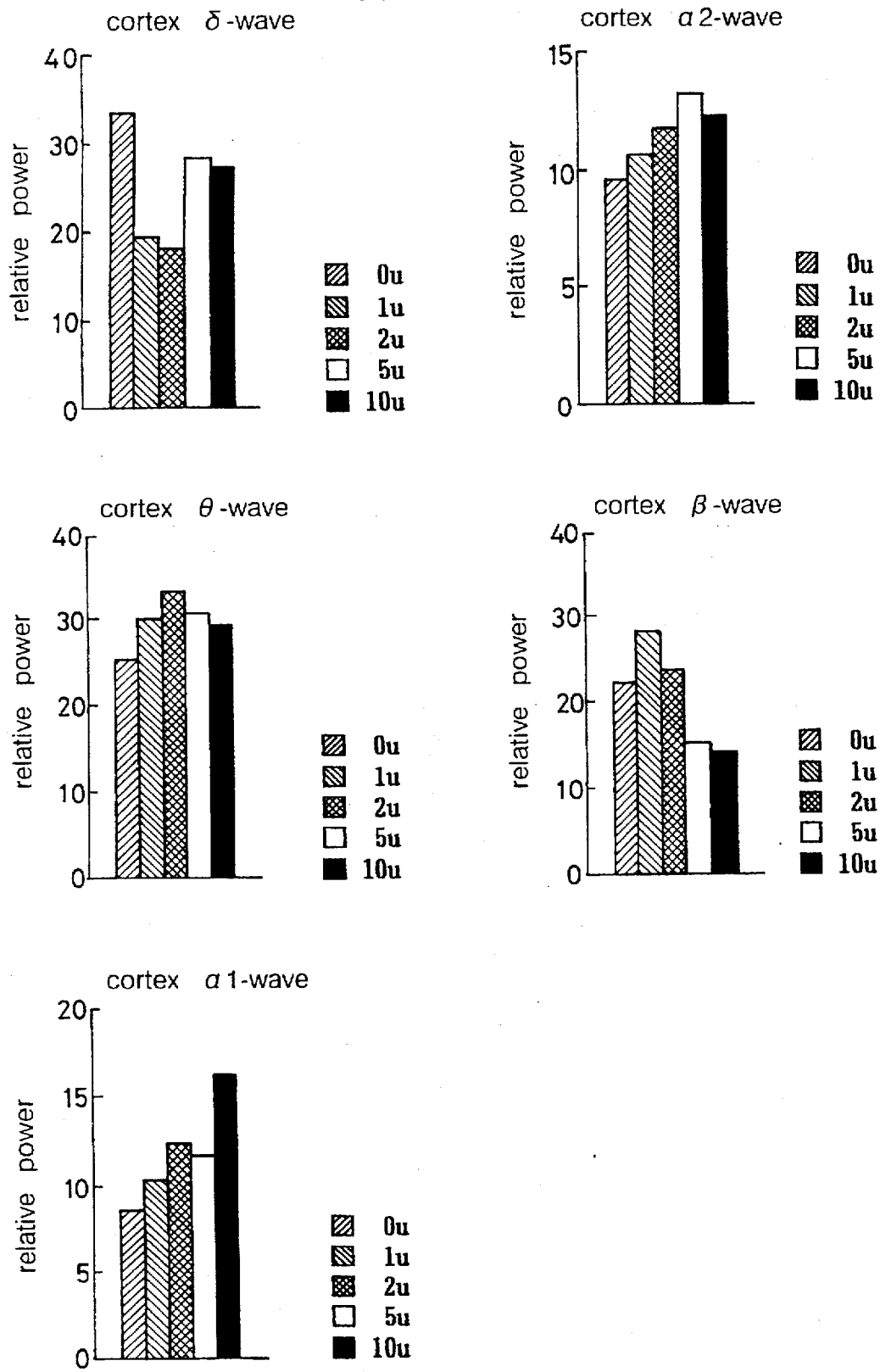
FIG. 1 is a view showing the relative power of δ-wave, θ-wave, α1-wave and β-wave in the cortex after 15 minutes since theanine administration in various doses.
Figure 2:
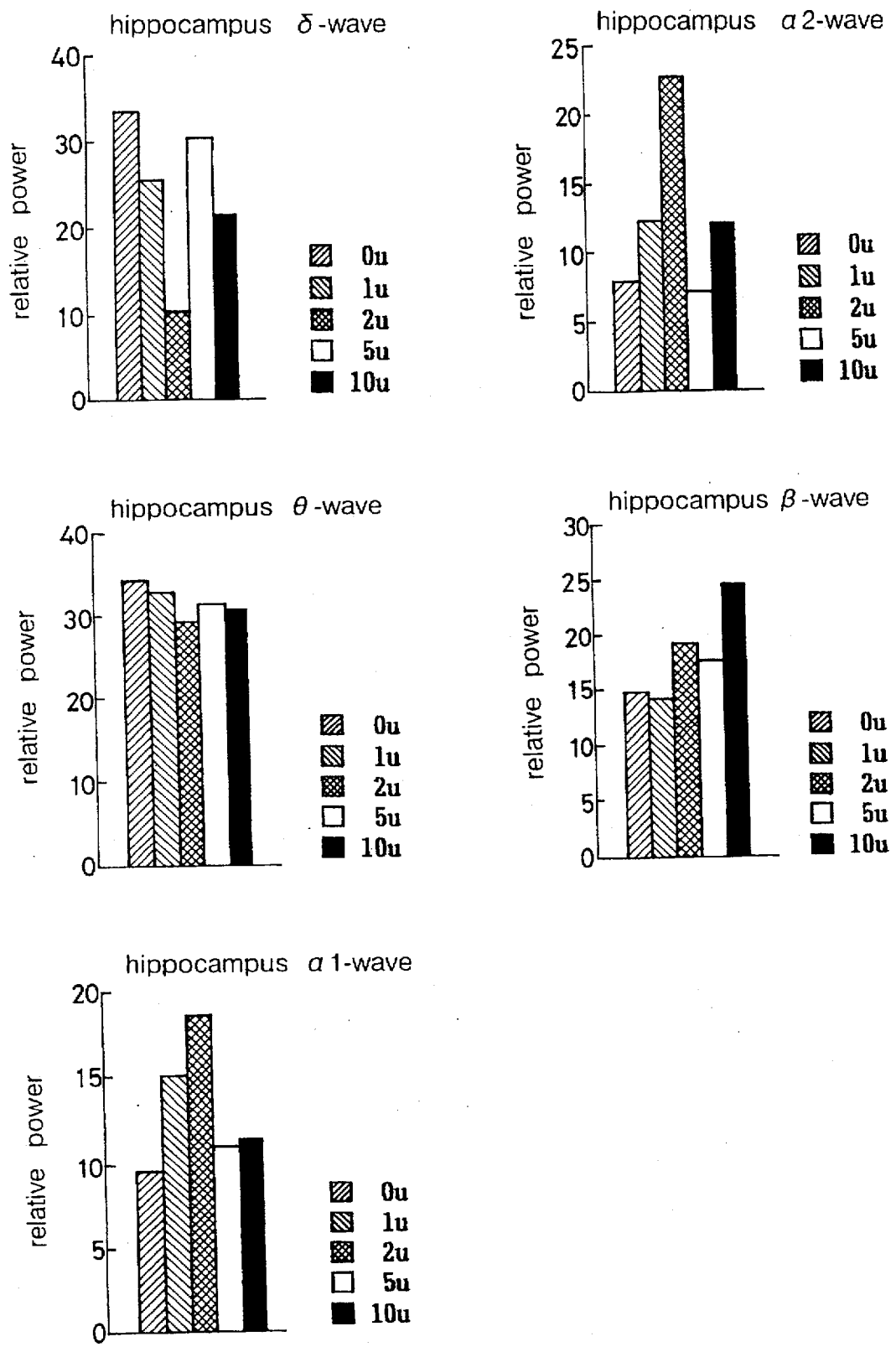
FIG. 2 is a view showing the relative power of δ-wave, θ-wave, α1-wave and β-wave in the hippocampus after 15 minutes since theanine administration in various doses.
Figure 3:
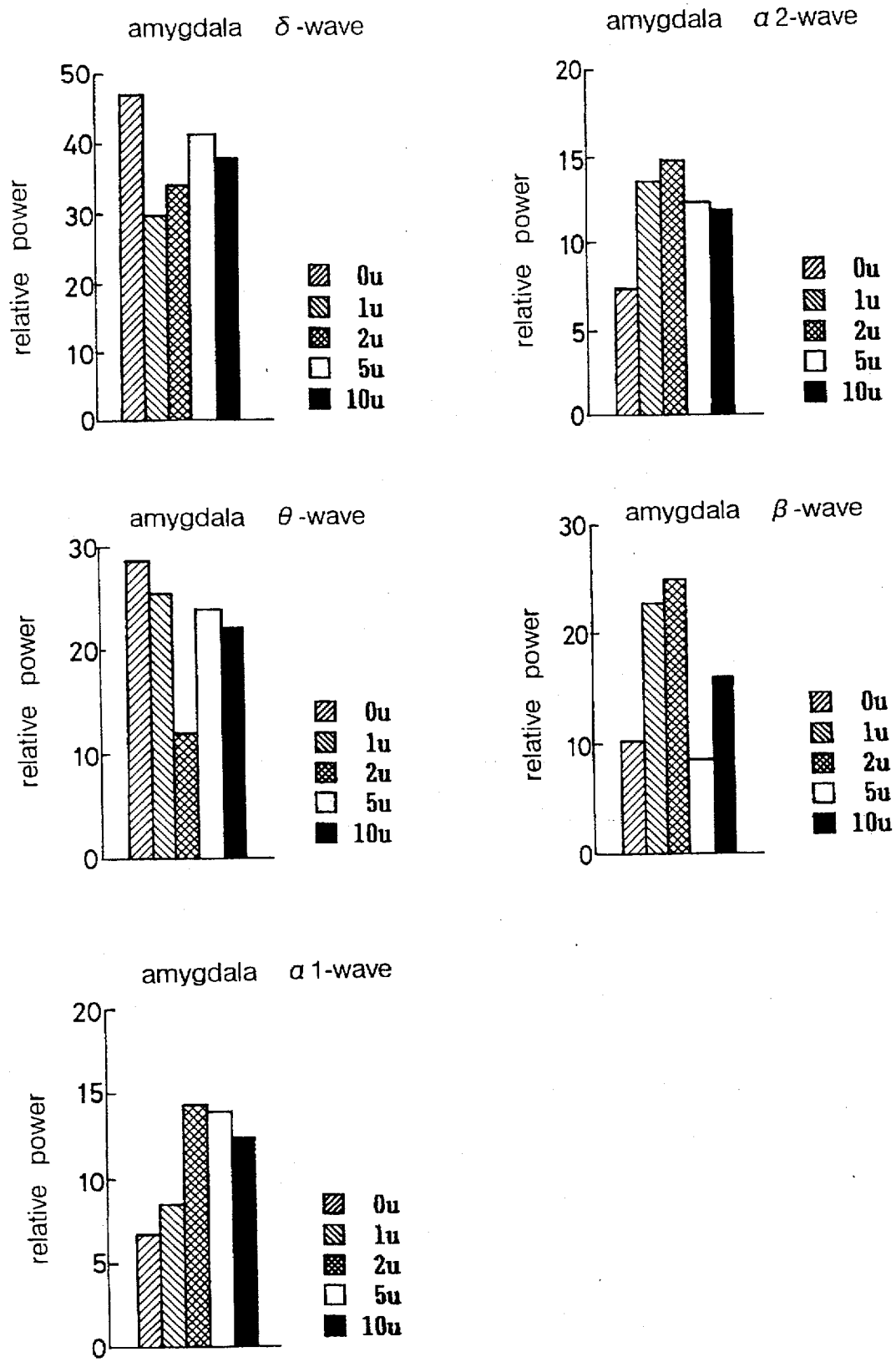
FIG. 3 is a view showing the relative power of δ-wave, θ-wave, α1-wave and β-wave in the amygdala after 15 minutes since theanine administration in various doses.
Figure 4:
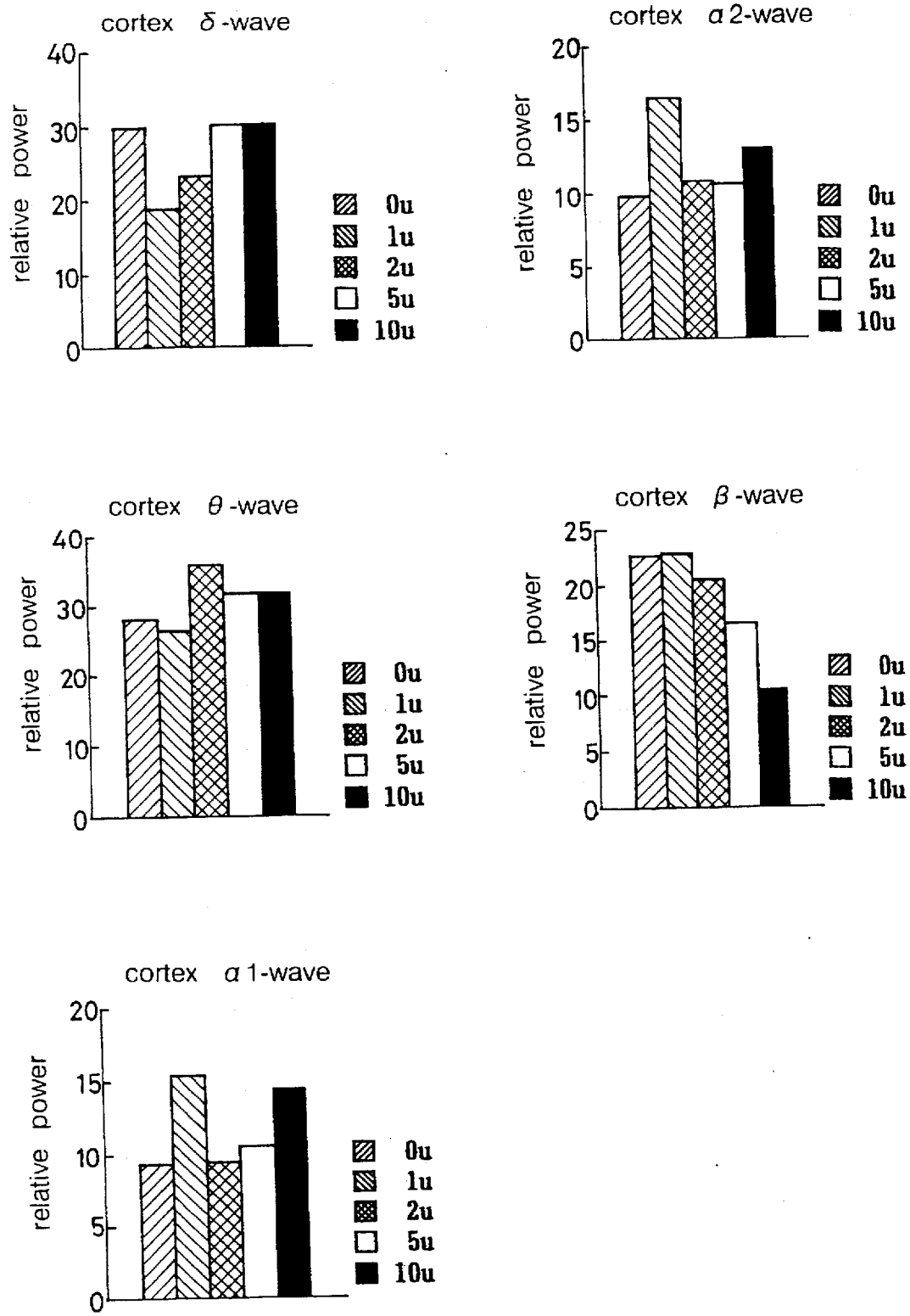
FIG. 4 is a view showing the relative power of δ-wave, θ-wave, α1-wave, α2-wave and β-wave in the cortex after 30 minutes since theanine administration in various doses.
Figure 5:
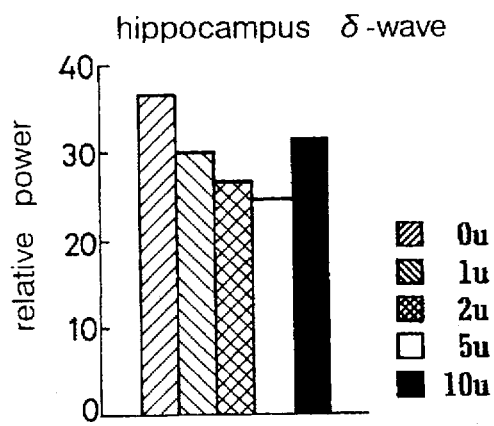
FIG. 5 is a view showing the relative power of δ-wave, θ-wave, α1-wave, α2-wave and β-wave in the hippocampus after 30 minutes since theanine administration in various doses.
Figure 5:
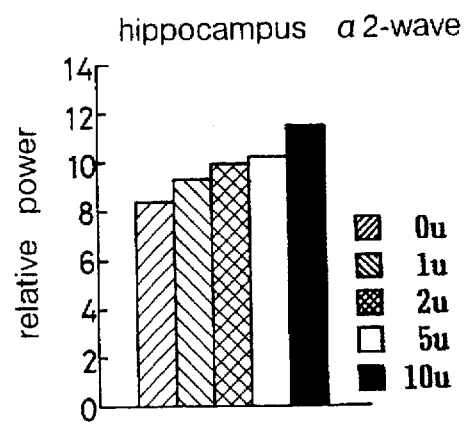
Figure 5:
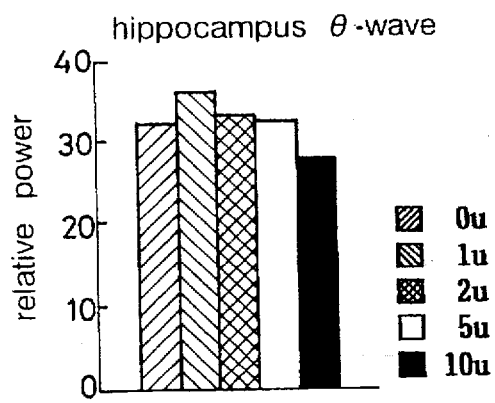
Figure 5:
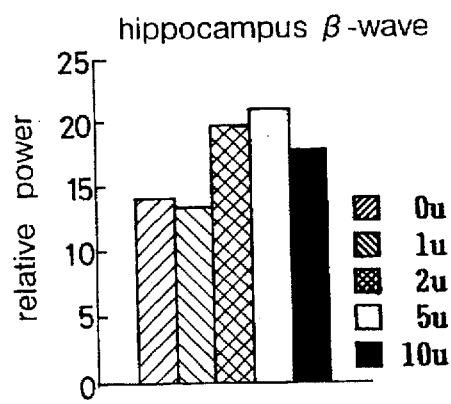
Figure 5:
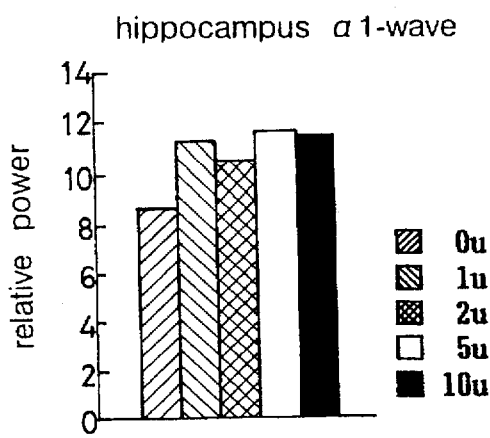
Figure 6:
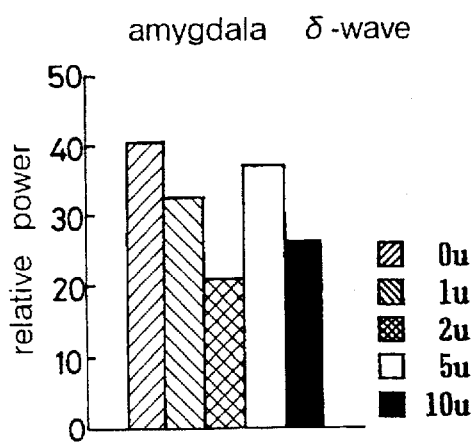
FIG. 6 is a view showing the relative power of δ-wave, θ-wave, α1-wave, α2-wave and β-wave in the amygdala after 30 minutes since theanine administration in various doses.
Figure 6:
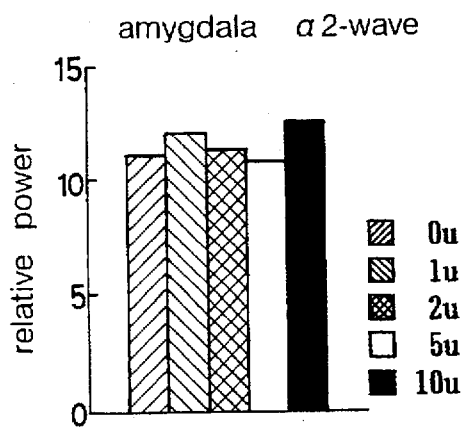
Figure 6:
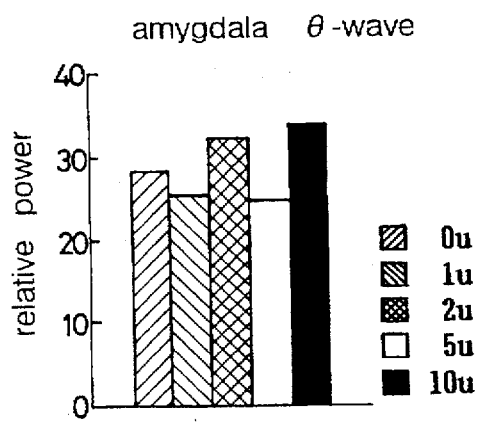
Figure 6:
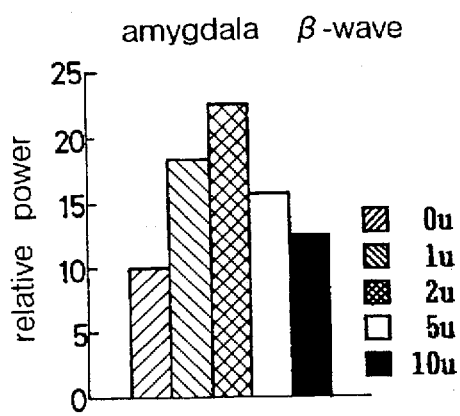
Figure 6:
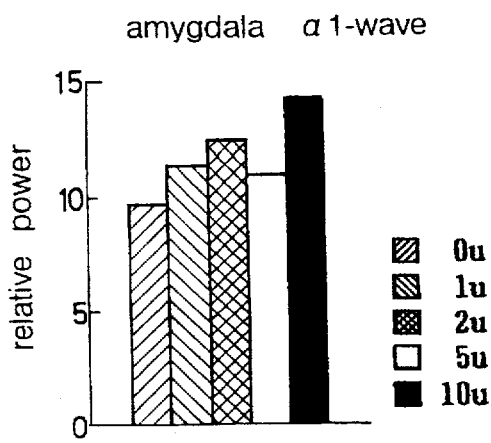
Figure 7:
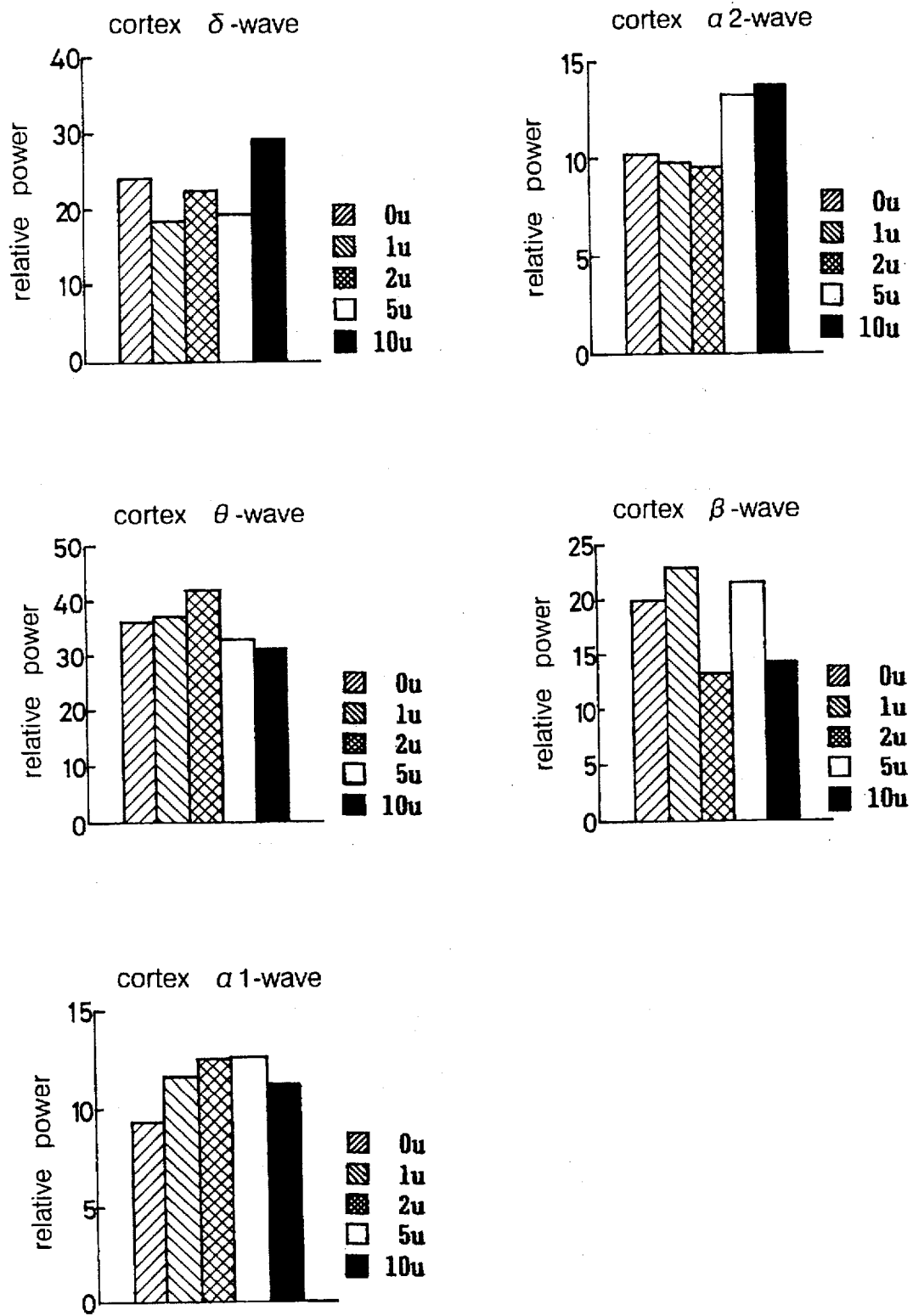
FIG. 7 is a view showing the relative power of δ-wave, θ-wave, α1-wave, α2-wave and β-wave in the cortex after 60 minutes since theanine administration in various doses.
Figure 8:
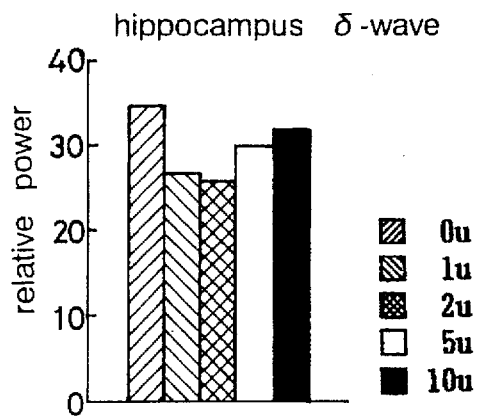
FIG. 8 is a view showing the relative power of δ-wave, θ-wave, α1-wave, α2-wave and β-wave in the hippocampus after 60 minutes since theanine administration in various doses.
Figure 8:
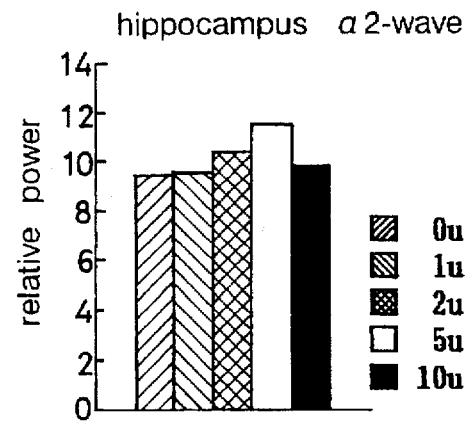
Figure 8:
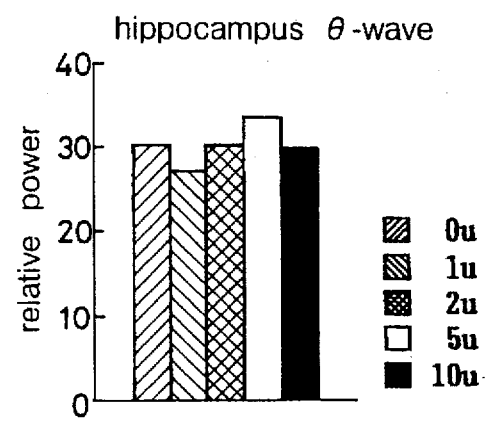
Figure 8:
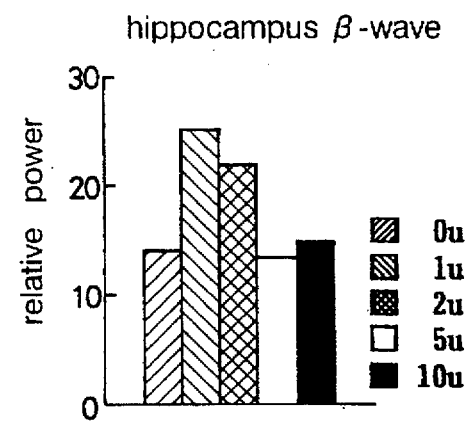
Figure 8:
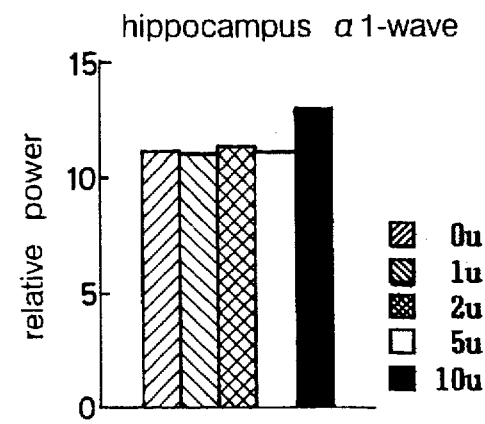
Figure 9:
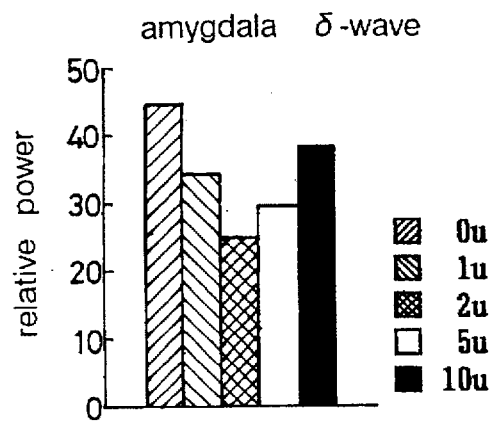
FIG. 9 is a view showing the relative power of δ-wave, θ-wave, α1-wave, α2-wave and β-wave in the amygdala after 60 minutes since theanine administration in various doses.
Figure 9:
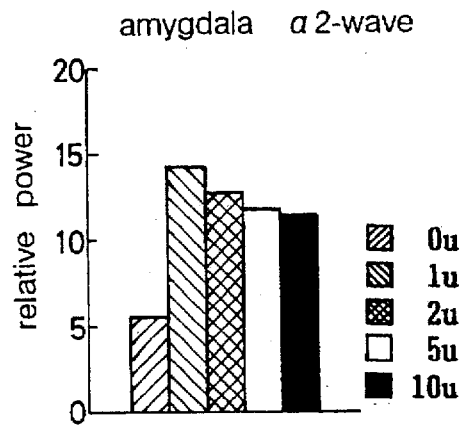
Figure 9:
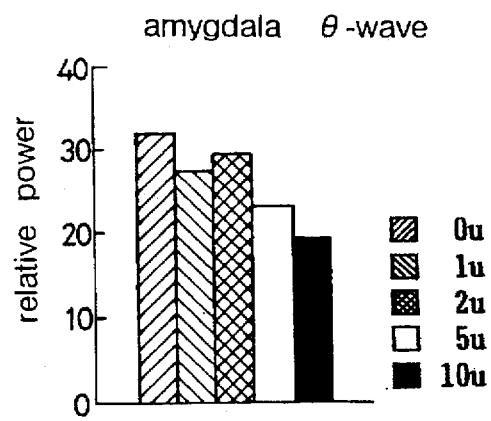
Figure 9:
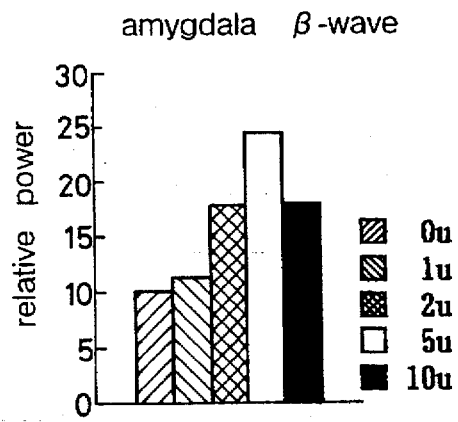
Figure 9:
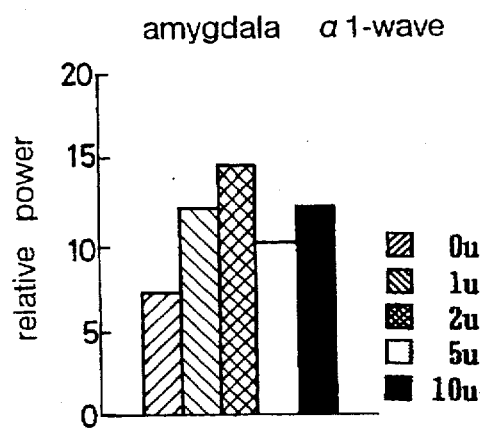
Figure 10:
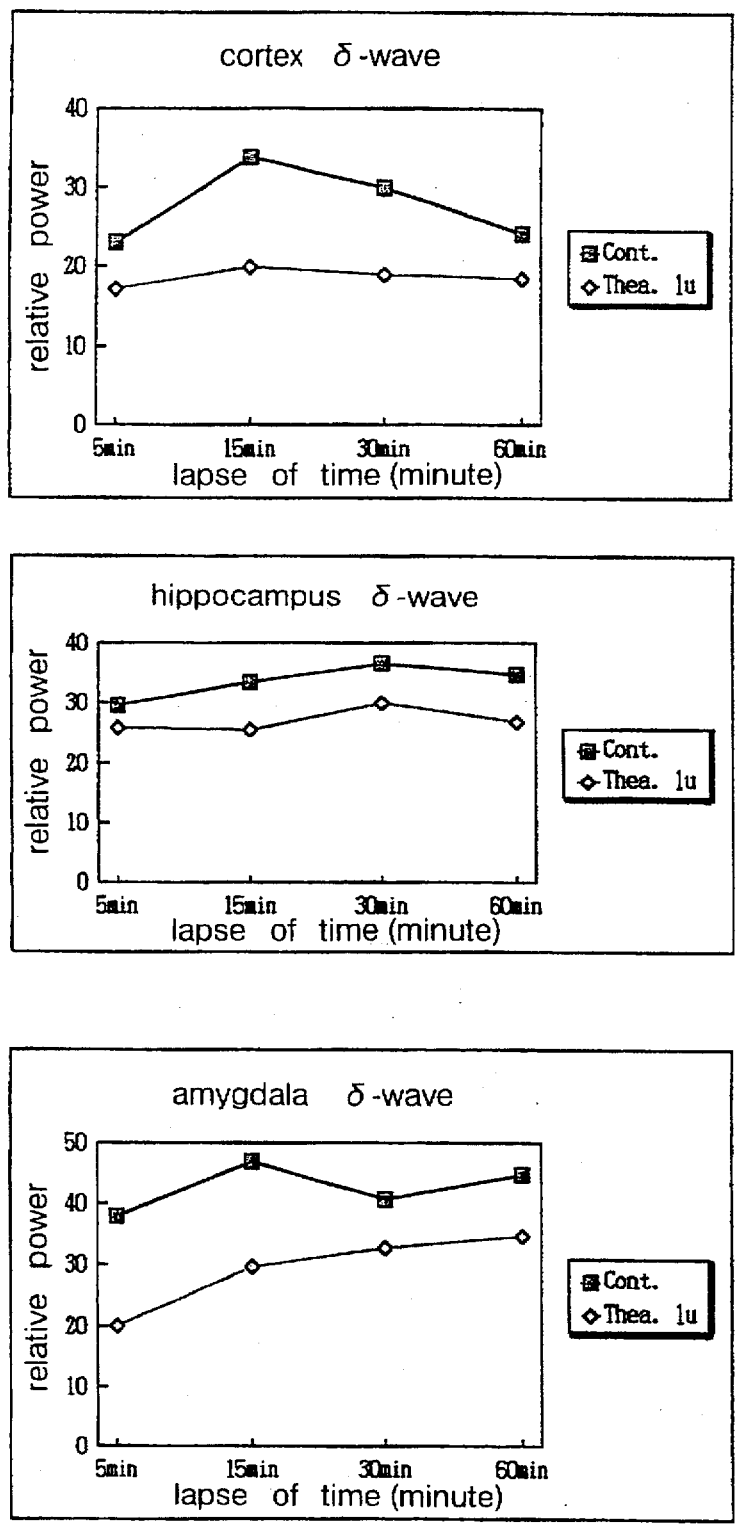
FIG. 10 is a view showing the change with lapse of time of the relative power of δ-wave in the cortex, the hippocampus and the amygdala when 1 μm of theanine is dosed.
Figure 11:
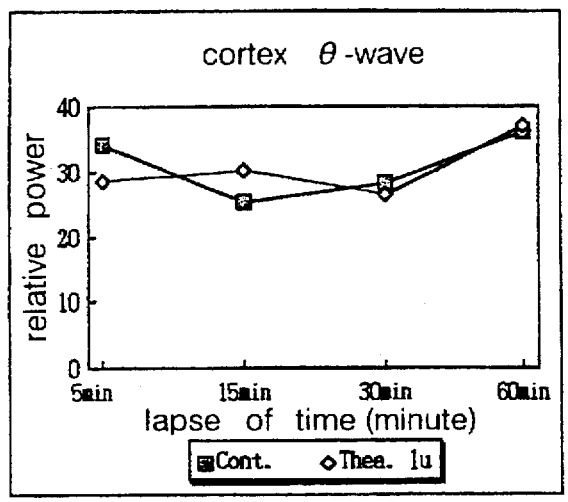
FIG. 11 is a view showing the change with lapse of time of the relative power of θ-wave in the cortex, the hippocampus and the amygdala when 1 μm of theanine is dosed.
Figure 11:
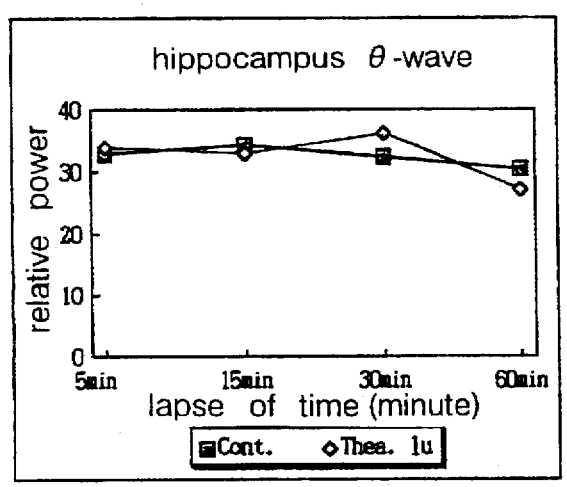
Figure 11:
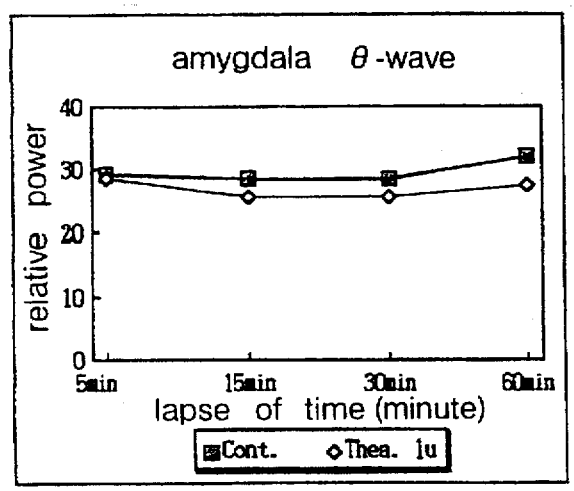
Figure 12:
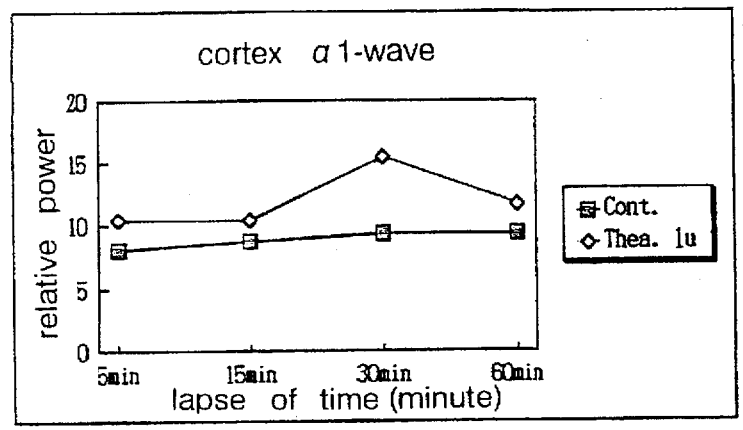
FIG. 12 is a view showing the change with lapse of time of the relative power of α1-wave in the cortex, the hippocampus and the amygdala when 1 μm of theanine is dosed.
Figure 12:
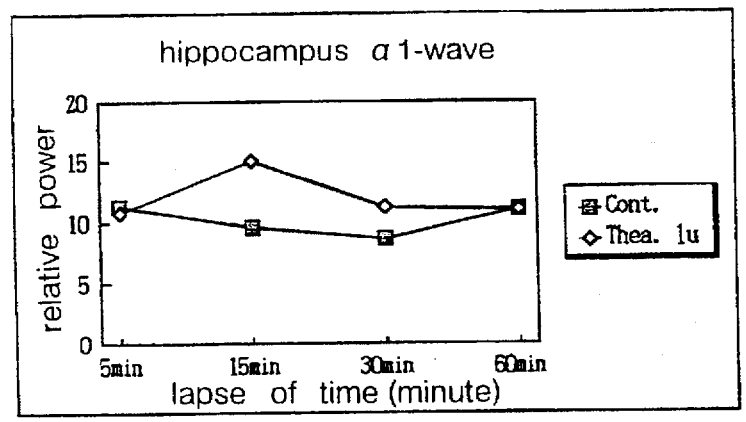
Figure 12:
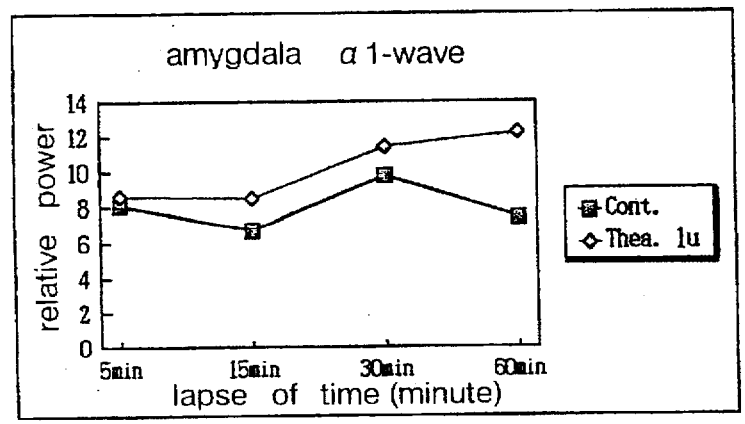
Figure 13:
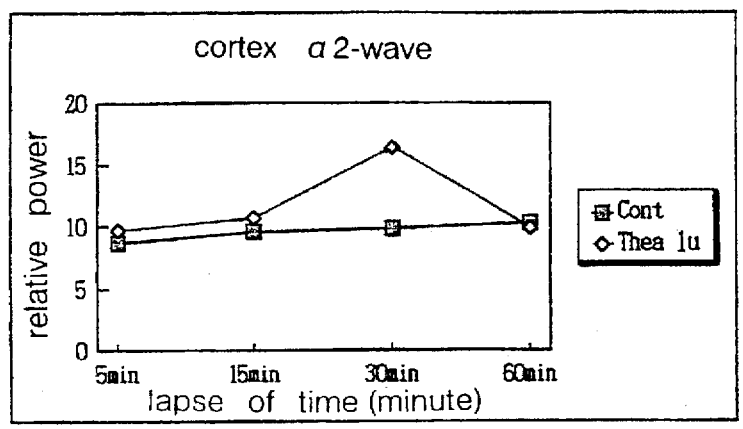
FIG. 13 is a view showing the change with lapse of time of the relative power of α2-wave in the cortex, the hippocampus and the amygdala when 1 μm of theanine is dosed.
Figure 13:
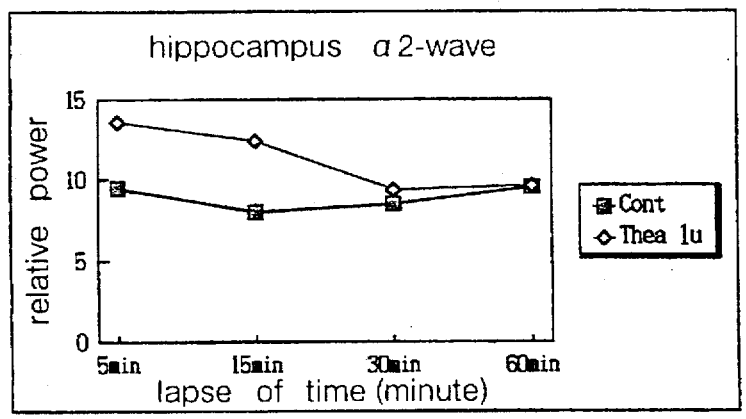
Figure 13:
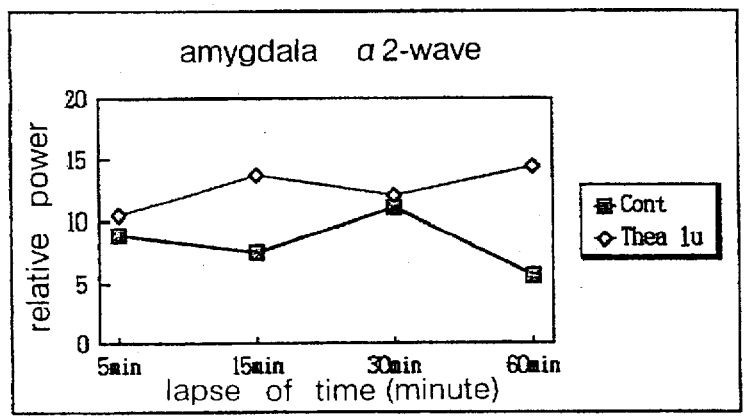
Figure 14:
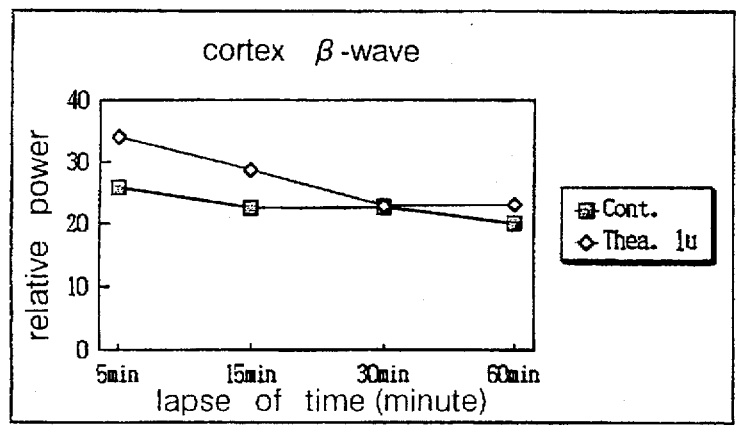
FIG. 14 is a view showing the change with lapse of time of the relative power of β-wave in the cortex, the hippocampus and the amygdala when 1 μm of theanine is dosed.
Figure 14:
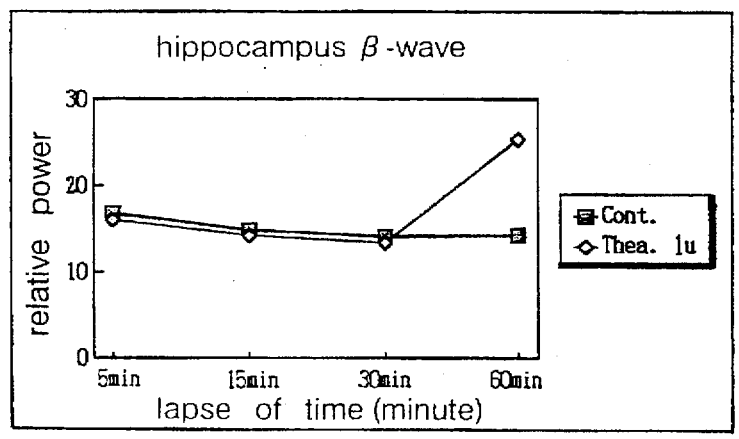
Figure 14:
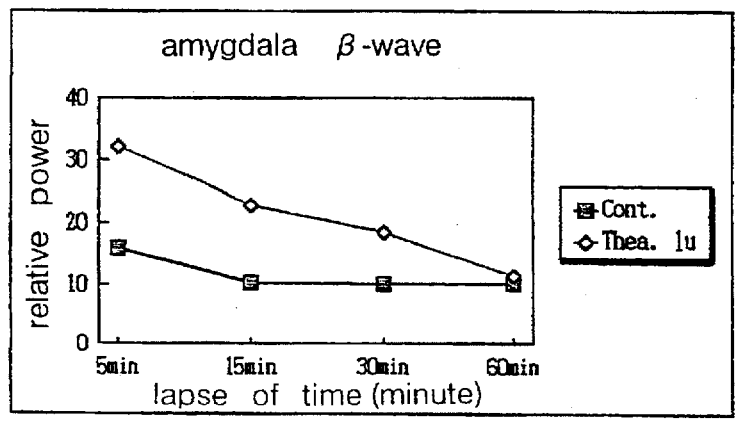
Figure 15:
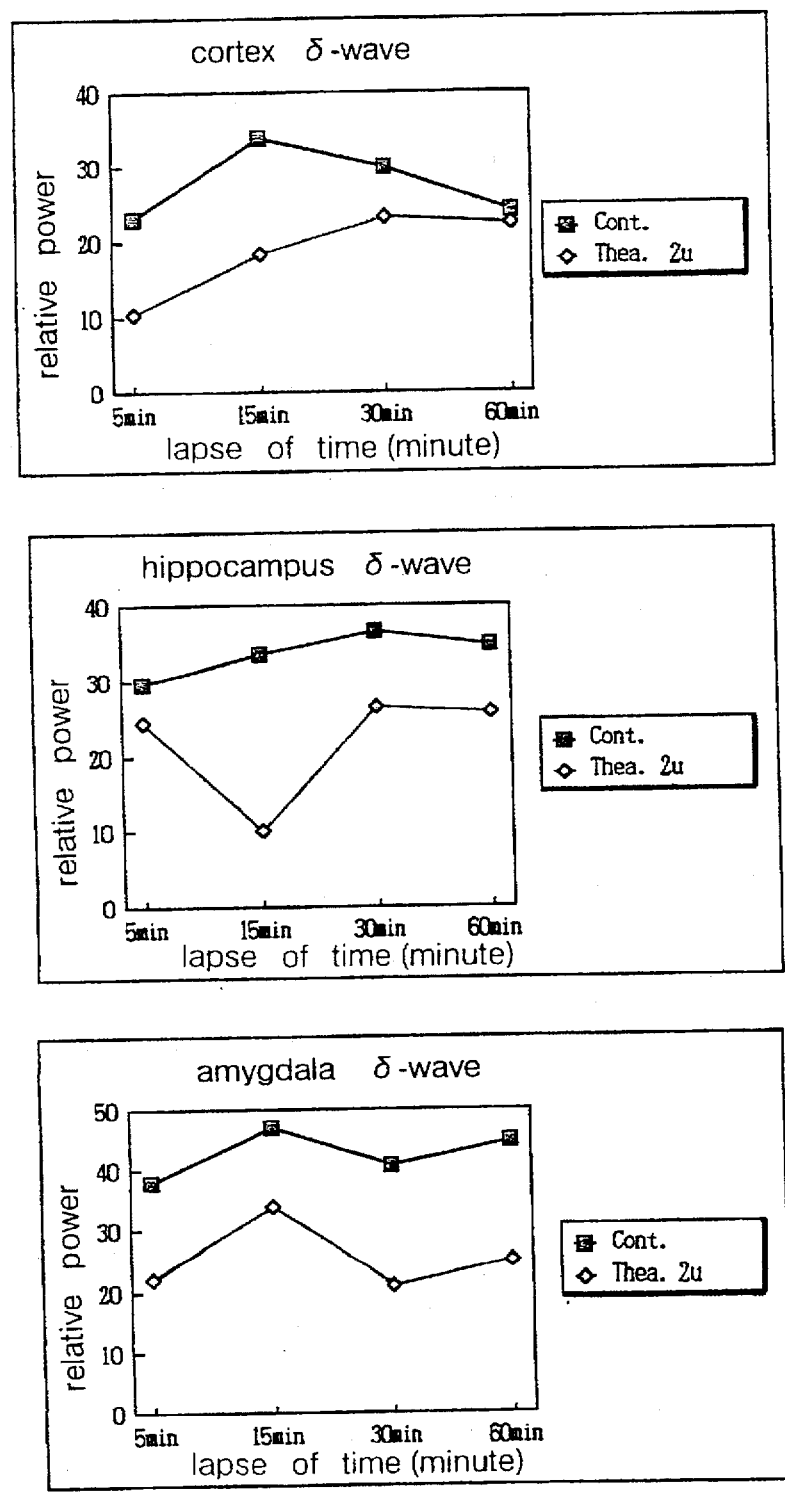
FIG. 15 is a view showing the change with lapse of time of the relative power of δ-wave in the cortex, the hippocampus and the amygdala when 2 μm of theanine is dosed.
Figure 16:
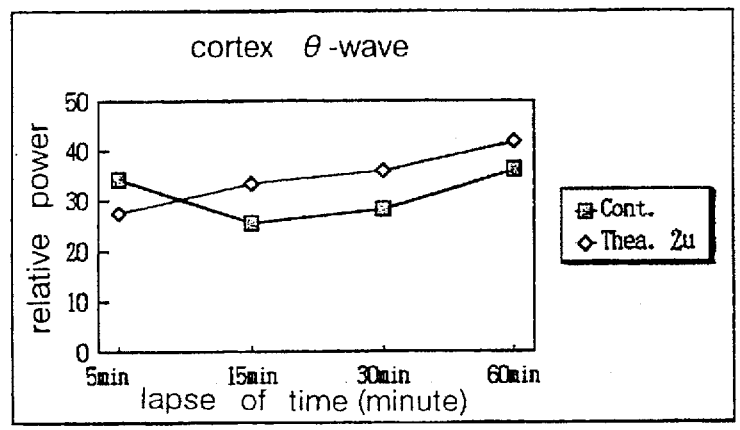
FIG. 16 is a view showing the change with lapse of time of the relative power of θ-wave in the cortex, the hippocampus and the amygdala when 2 μm of theanine is dosed.
Figure 16:
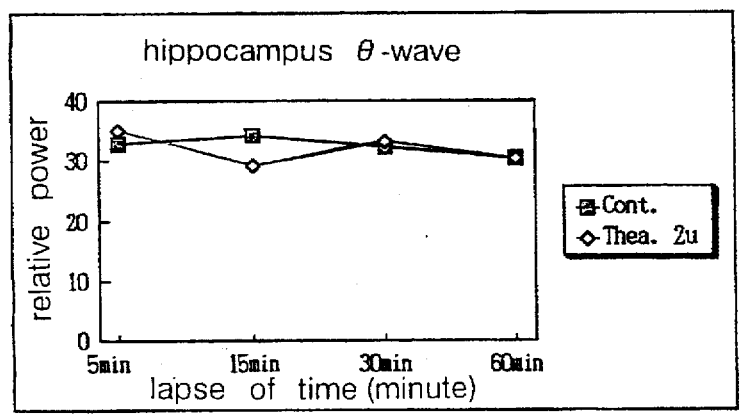
Figure 16:
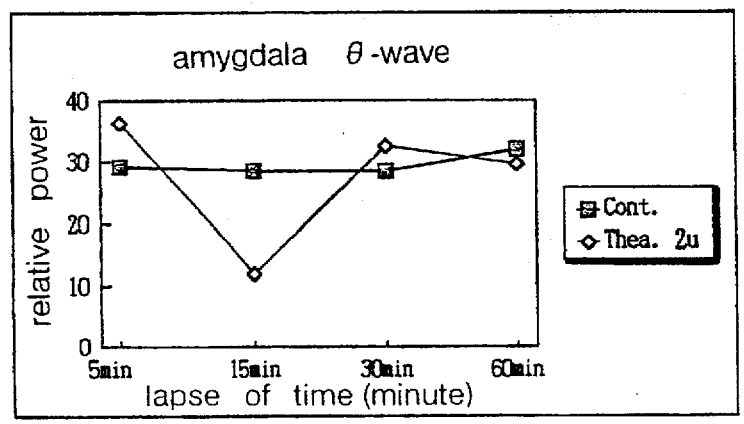
Figure 17:
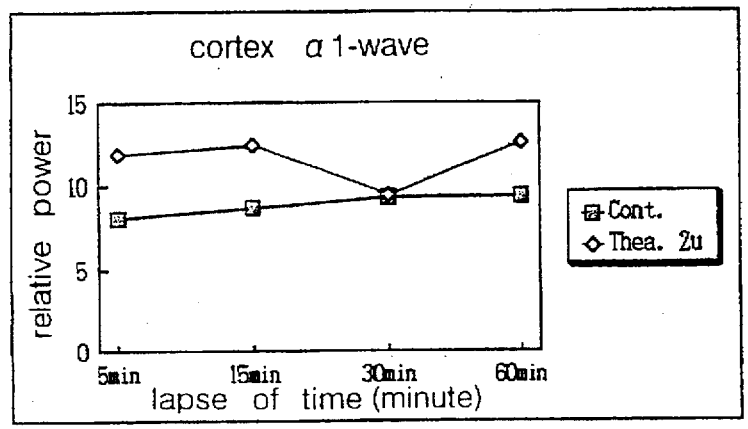
FIG. 17 is a view showing the change with lapse of time of the relative power of α1-wave in the cortex, the hippocampus and the amygdala when 2 μm of theanine is dosed.
Figure 17:
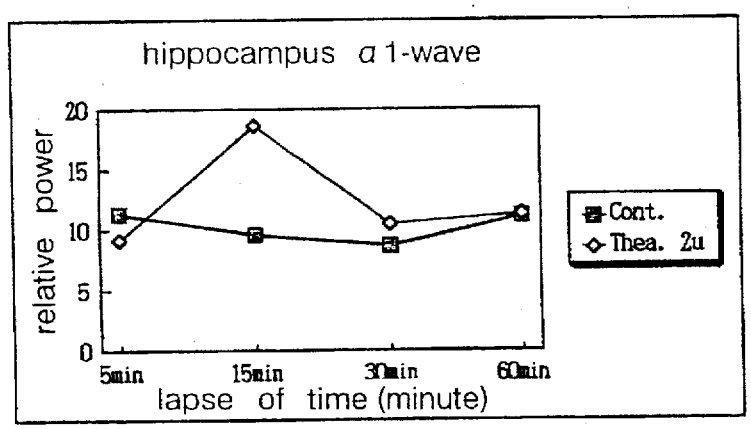
Figure 17:
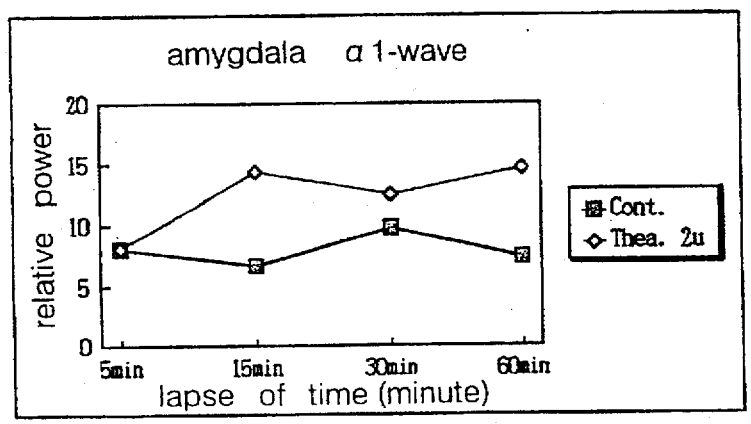
Figure 18:
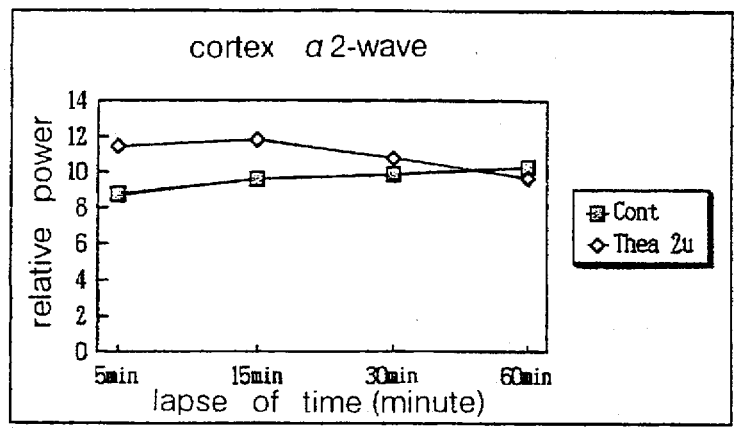
FIG. 18 is a view showing the change with lapse of time of the relative power of α2-wave in the cortex, the hippocampus and the amygdala when 2 μm of theanine is dosed.
Figure 18:
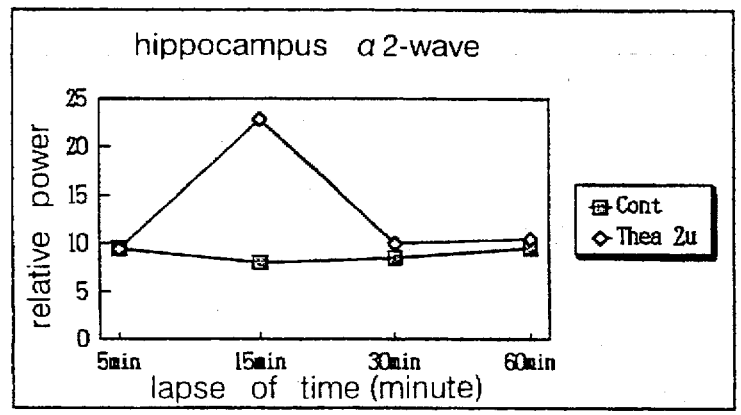
Figure 18:
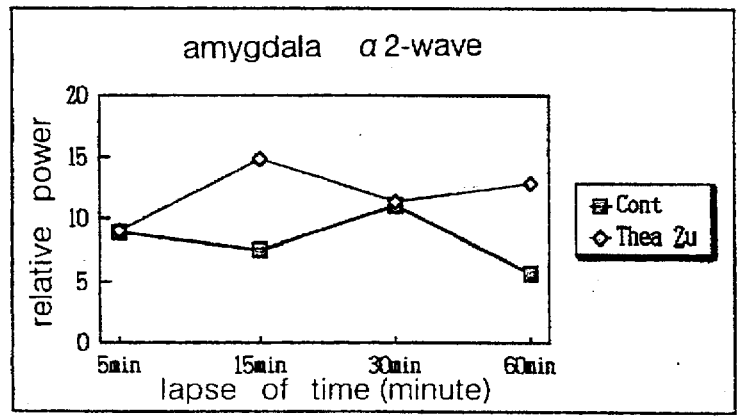
Figure 19:
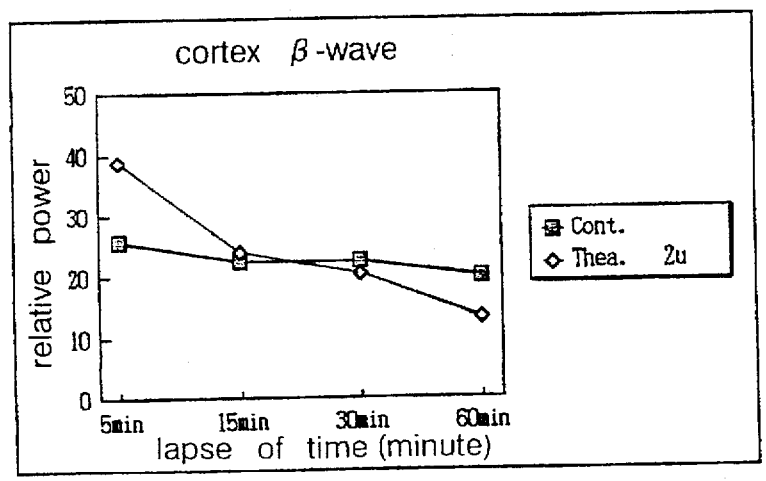
FIG. 19 is a view showing the change with lapse of time of the relative power of β-wave in the cortex, the hippocampus and the amygdala when 2 μm of theanine is dosed.
Figure 19:
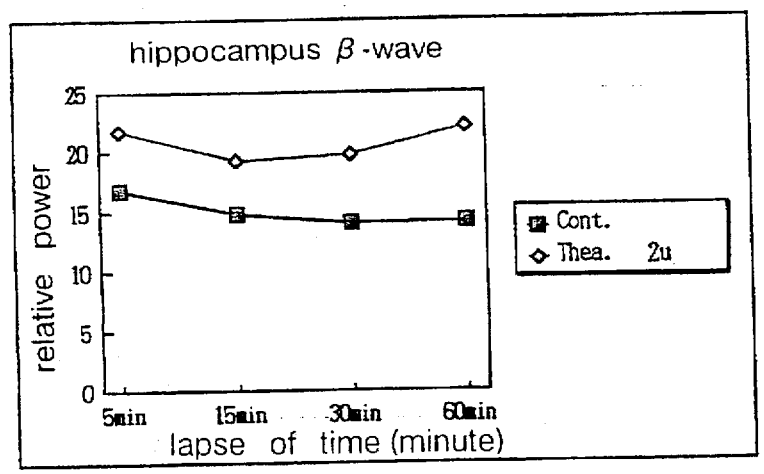
Figure 19:
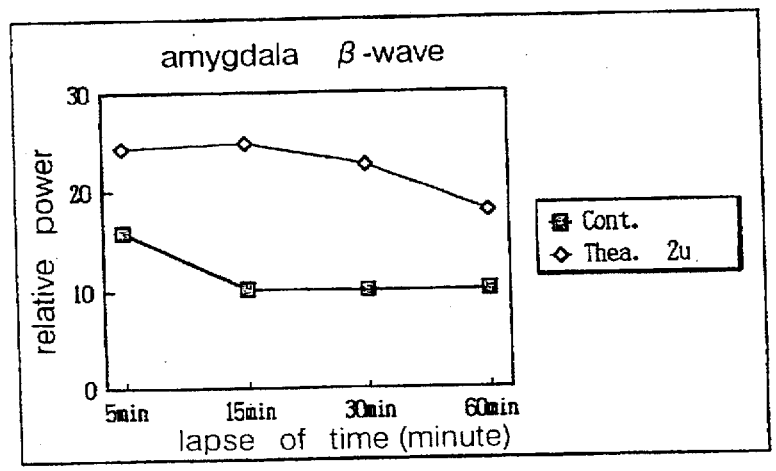
Figure 20:
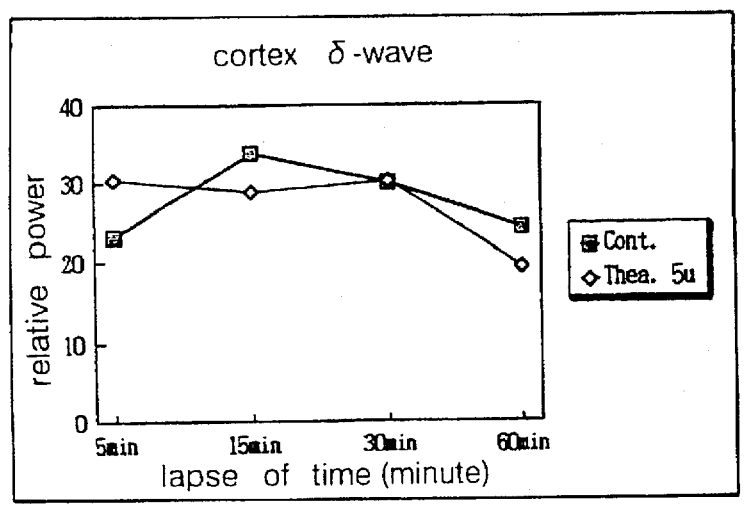
FIG. 20 is a view showing the change with lapse of time of the relative power of δ-wave in the cortex, the hippocampus and the amygdala when 5 μm of theanine is dosed.
Figure 20:
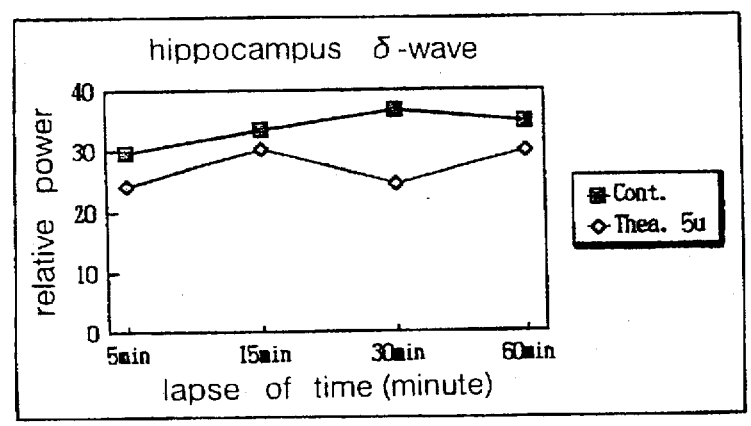
Figure 20:
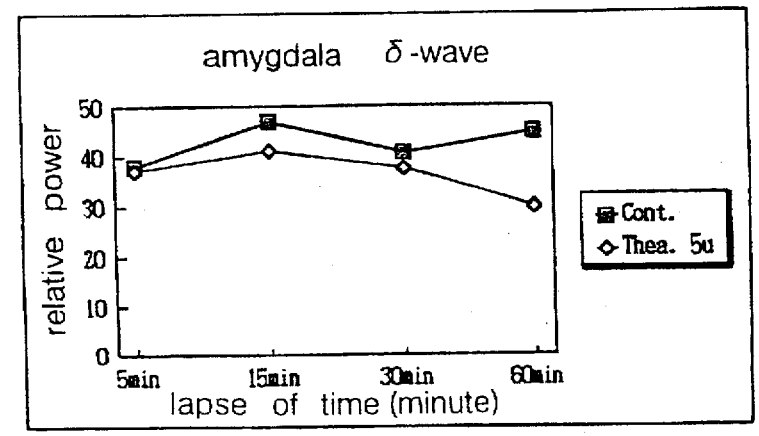
Figure 21:
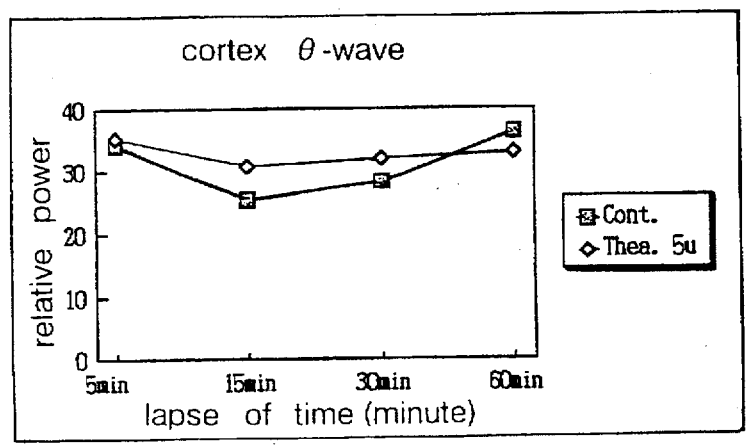
FIG. 21 is a view showing the change with lapse of time of the relative power of θ-wave in the cortex, the hippocampus and the amygdala when 5 μm of theanine is dosed.
Figure 21:
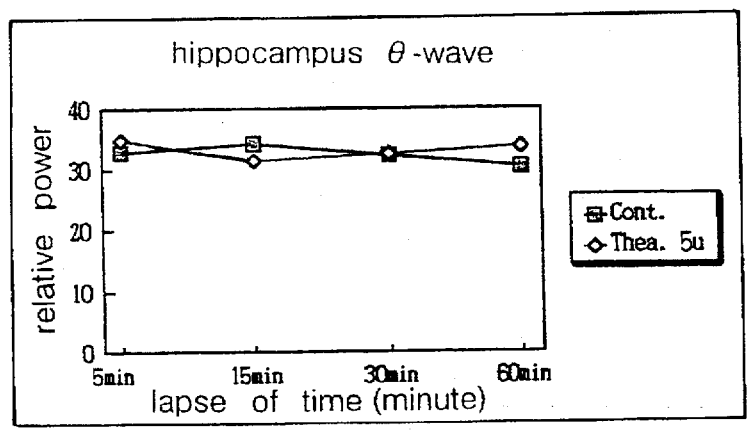
Figure 21:
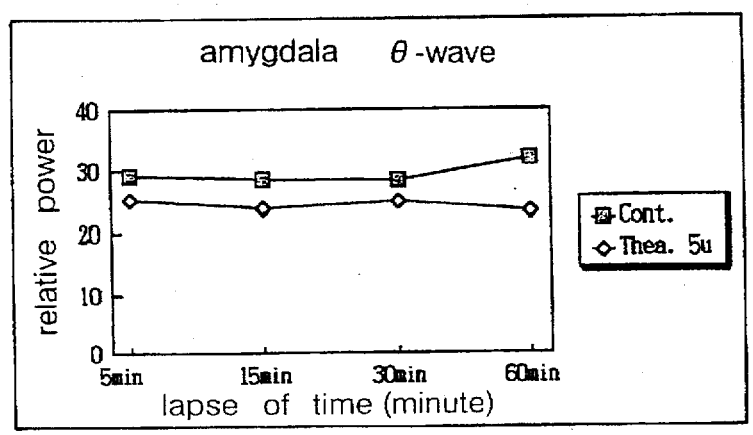
Figure 22:
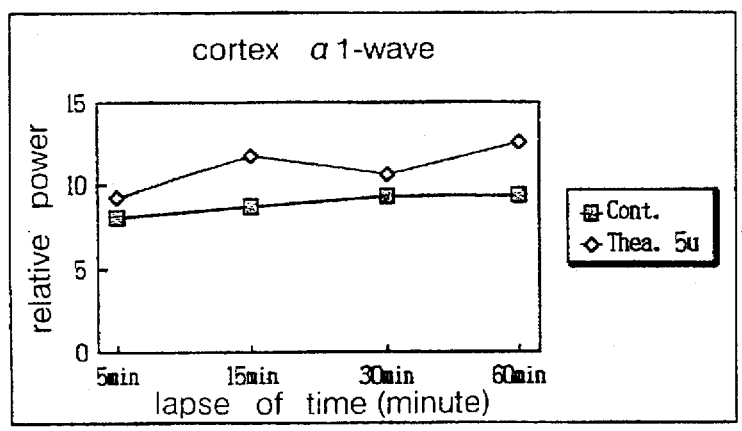
FIG. 22 is a view showing the change with lapse of time of the relative power of α1-wave in the cortex, the hippocampus and the amygdala when 5 μm of theanine is dosed.
Figure 22:
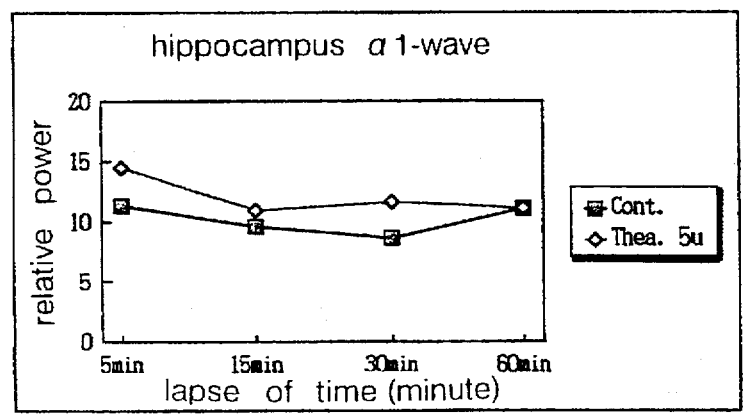
Figure 22:
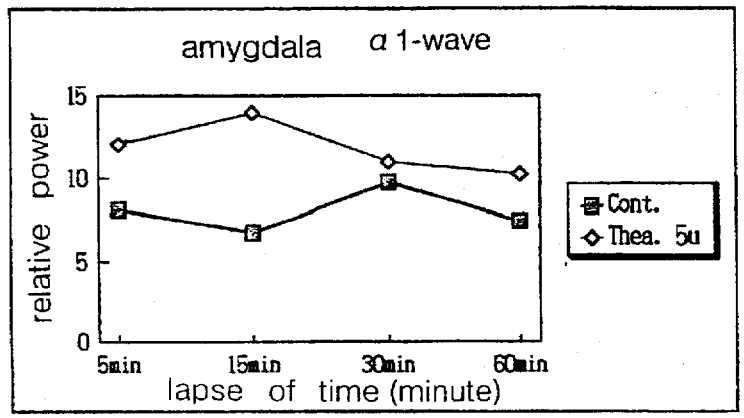
Figure 23:
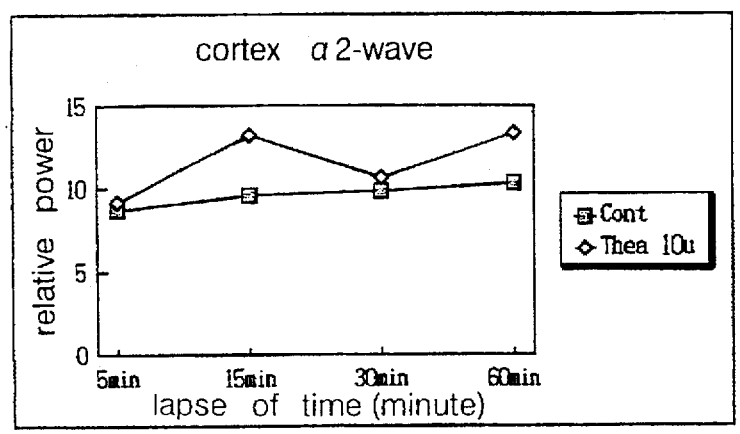
FIG. 23 is a view showing the change with lapse of time of the relative power of α2-wave in the cortex, the hippocampus and the amygdala when 5 μm of theanine is dosed.
Figure 23:
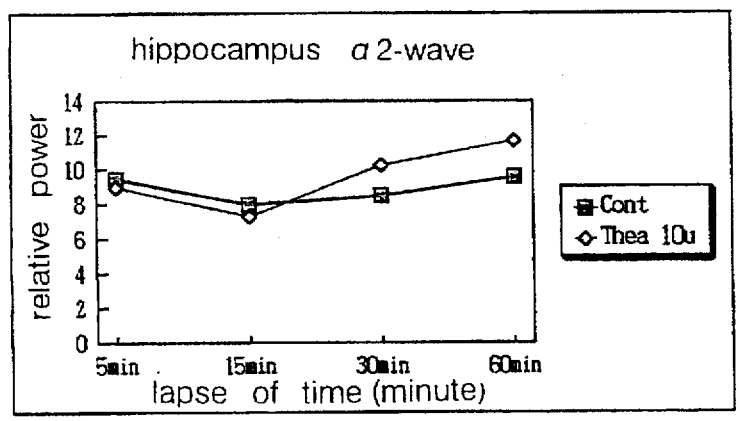
Figure 23:
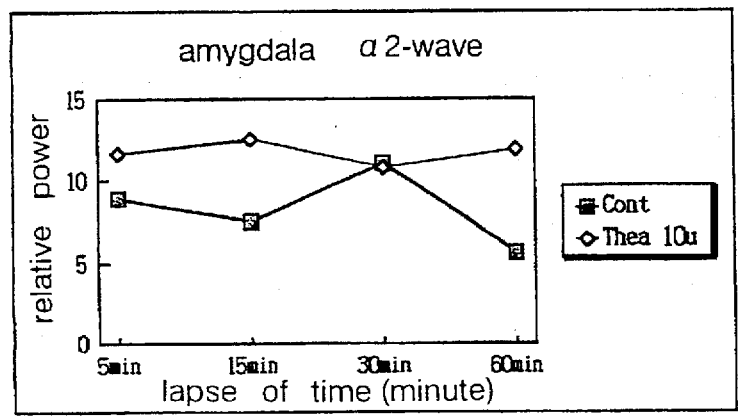
Figure 24:
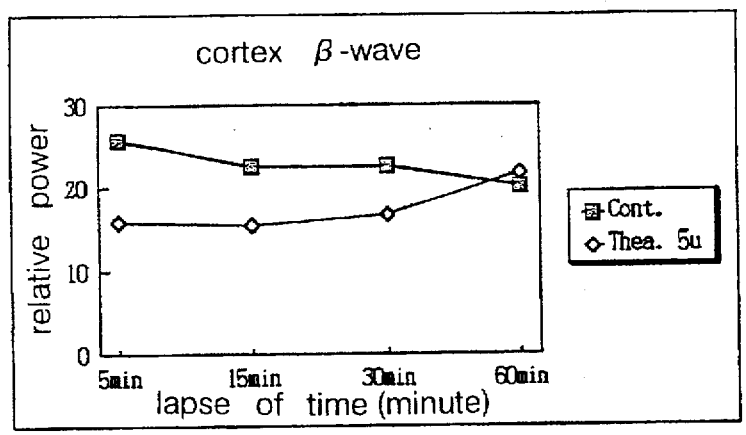
FIG. 24 is a view showing the change with lapse of time of the relative power of β-wave in the cortex, the hippocampus and the amygdala when 5 μm of theanine is dosed.
Figure 24:
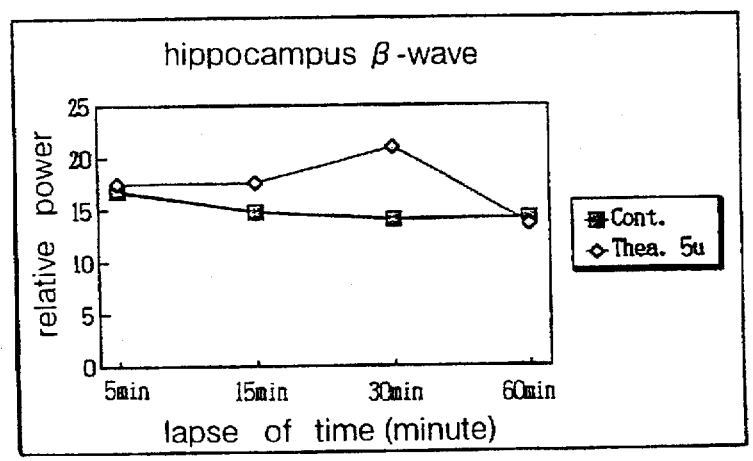
Figure 24:
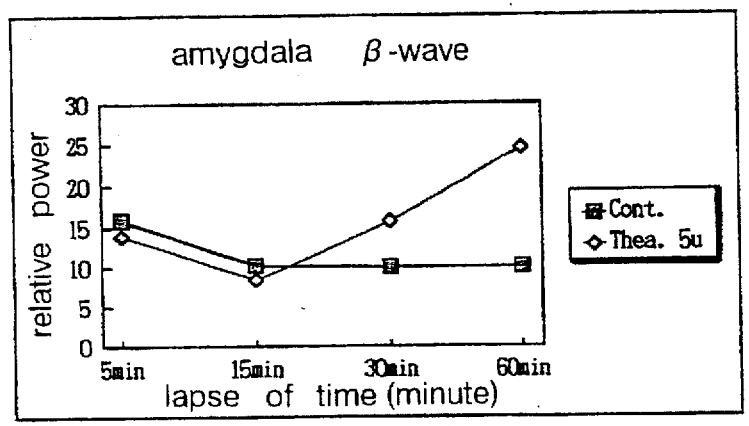
Figure 25:
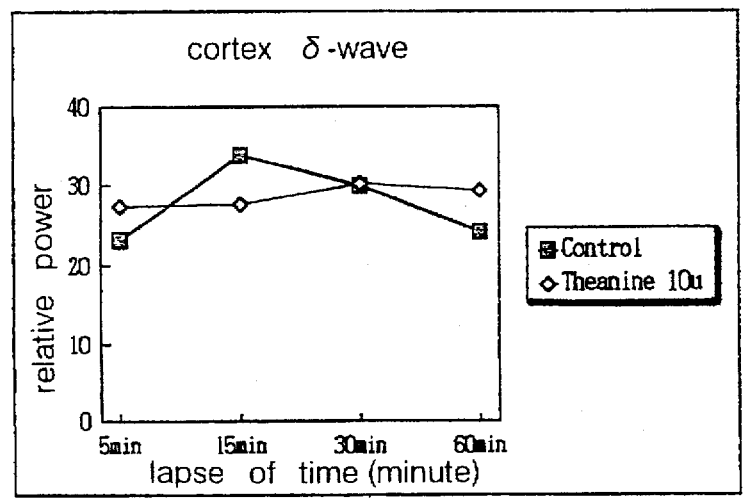
FIG. 25 is a view showing the change with lapse of time of the relative power of δ-wave in the cortex, the hippocampus and the amygdala when 10 μm of theanine is dosed.
Figure 25:
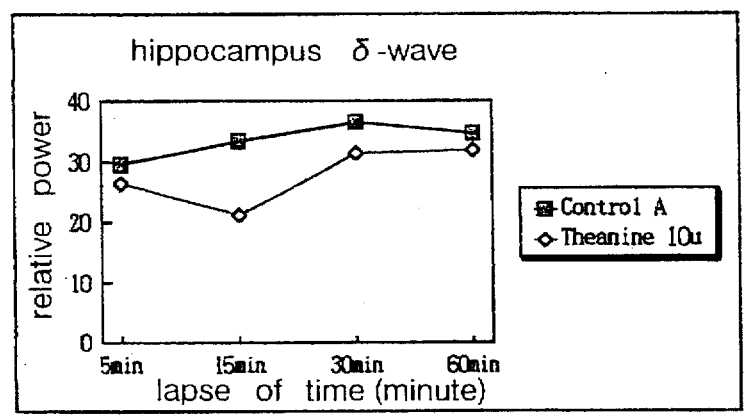
Figure 25:
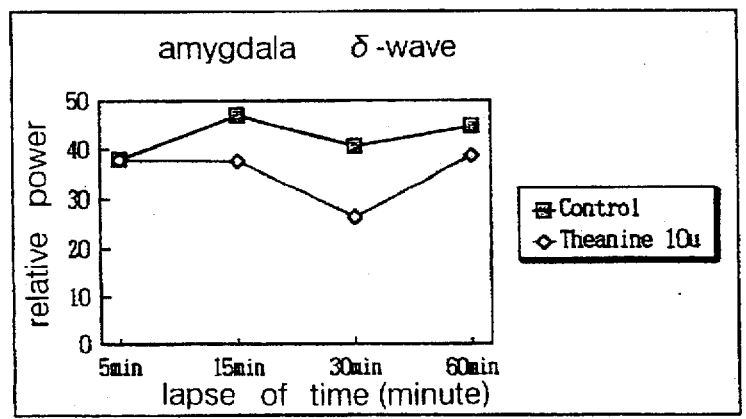
Figure 26:
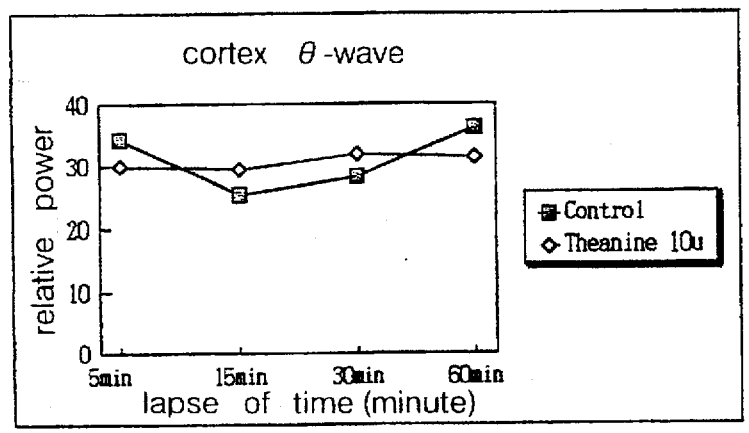
FIG. 26 is a view showing the change with lapse of time of the relative power of θ-wave in the cortex, the hippocampus and the amygdala when 10 μm of theanine is dosed.
Figure 26:
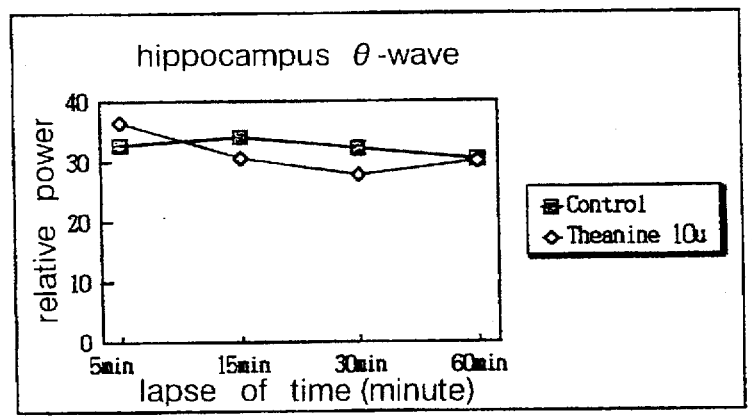
Figure 26:
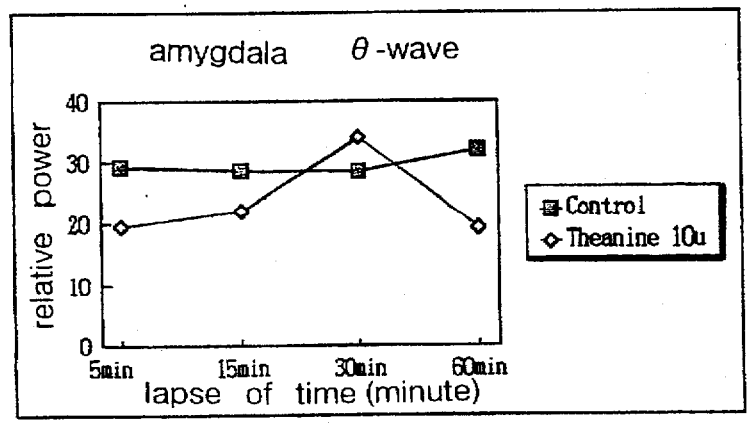
Figure 27:
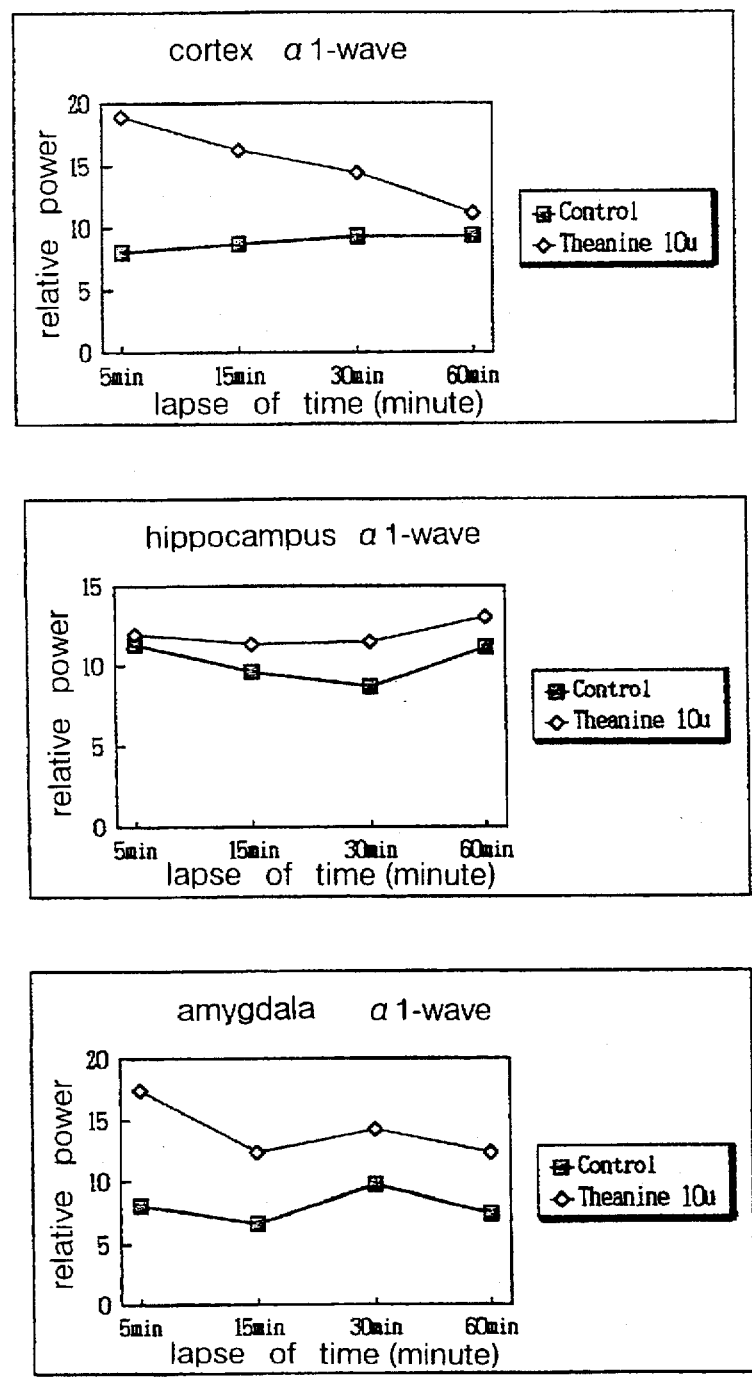
FIG. 27 is a view showing the change with lapse of time of the relative power of α1-wave in the cortex, the hippocampus and the amygdala when 10 μm of theanine is dosed.
Figure 28:
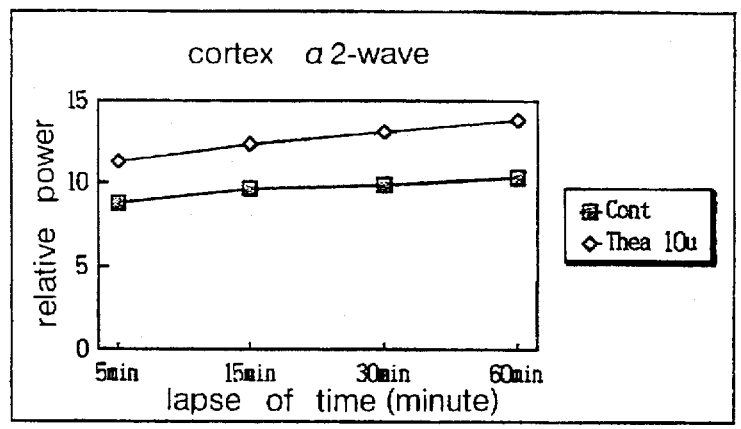
FIG. 28 is a view showing the change with lapse of time of the relative power of α2-wave in the cortex, the hippocampus and the amygdala when 10 μm of theanine is dosed.
Figure 28:
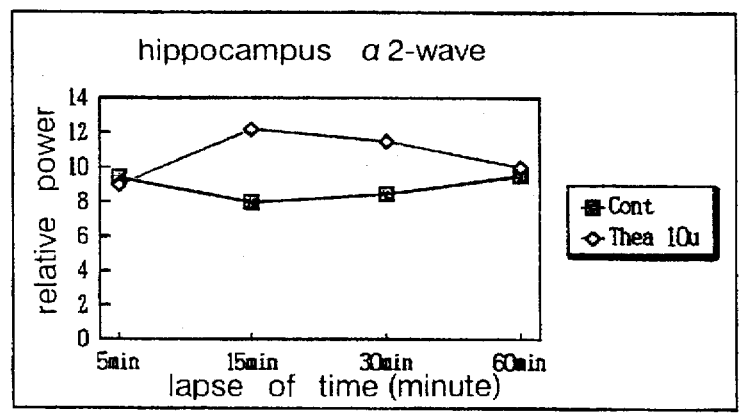
Figure 28:
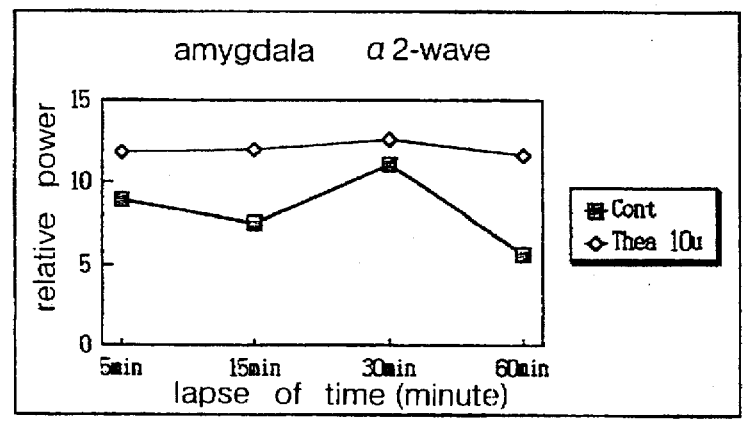
Figure 29:
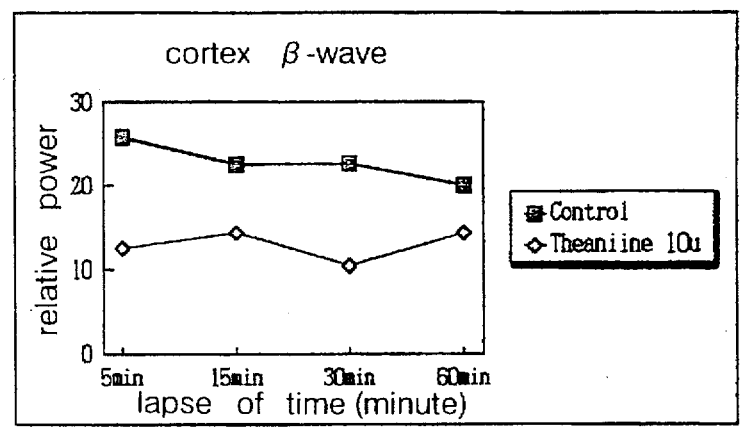
FIG. 29 is a view showing the change with lapse of time of the relative power of β-wave in the cortex, the hippocampus and the amygdala when 10 μm of theanine is dosed.
Figure 29:
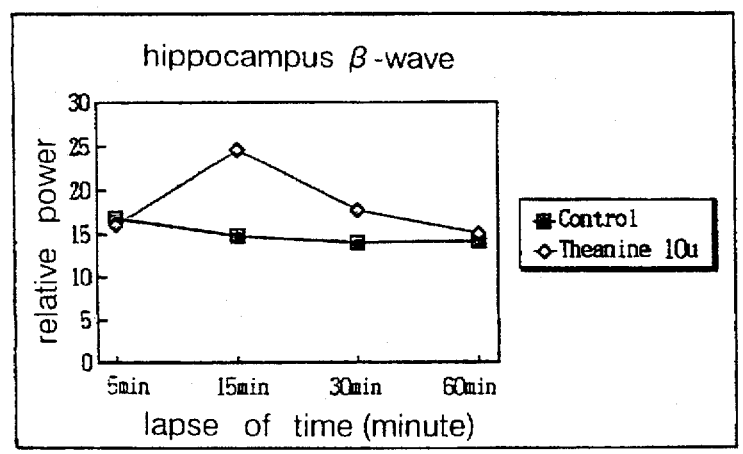
Figure 29:
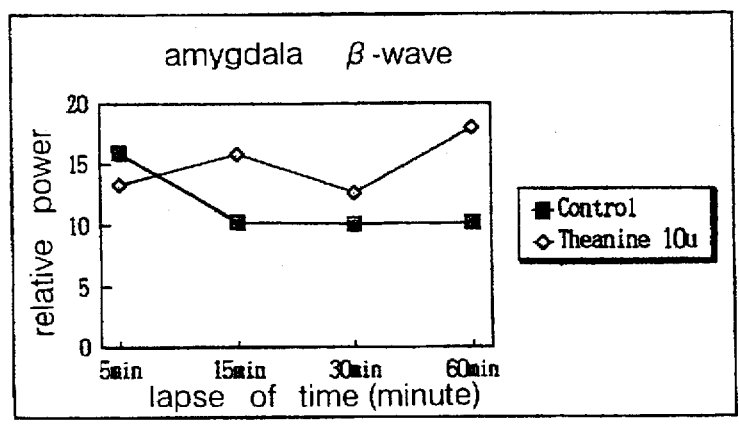

As shown in Experiment 1 described below, when theanine was dosed by an intravenous injection, it was found that the excitement accelerating action could be obtained in a range of from 1 μmol/kg (0.17 mg/kg) to 5 μmol/kg (0.85 mg/kg) based on the weight, and preferably from 1 μmol/kg (0.17 mg/kg) to 2 μmol/kg (0.34 mg/kg) based on the weight. Therefore, when it is dosed as an injection agent, the range that theanine shows the excitement accelerating action is considered to be the range which contains theanine of from 0.17 mg/kg to 0.85 mg/kg, preferably from 0.17 mg/kg to 0.34 mg/kg based on the weight.

Furthermore, considering the result of said Experiment 1 and that the bioavailability of aminoacids mixture solution of which property is similar to that of theanine is from 30% to 83% (Nutritional Science Handbook, issued by Gihodo Shuppan, 1985), the minimum dose can be calculated as about 0.20 mg/kg (0.17/0.83), and the maximum dose as about 2.8 mg/kg (0.85/0.30). Therefore, the range that theanine dosed as an oral agent shows the excitement accelerating action is considered to be the range containing theanine from 0.20 mg/kg to 2.8 mg/kg based on the weight.

However, considering that the bioavailability of glutamic acids mixture solution of which property approximates to that of theanine is 33.8% ("Nutritional Science Handbook", issued by Gihodo Shuppan, 1985), the range that theanine dosed as an oral agent shows the excitement accelerating action is considered more preferably to be the range containing theanine from about 0.50 mg/kg to 2.5 mg/kg (0.17/0.338–0.85/0.338) based on the weight.

Therefore, it is considered that the very small amount in the range that said theanine shows the excitement accelerating action indicates from about 0.17 mg/kg to 2.8 mg/kg based on the weight, from the viewpoint of the effective range of said injection agent and oral agent. That is, when the weight of one person is assumed to be about 20 kg to 100 kg, it means the range of from about 3.4 mg to 280 mg per person.

Theanine in the present invention is contained in tea and the like, therefore it can be considered to be a harmless additive. Moreover, theanine can be produced, for example, by extracting tea leaves with organic solvent such as water, hot water or ethanol, or by chemical synthesis, by microbial fermentation, or by culture of vegetable tissues.

Furthermore, the excitement accelerating agent of the present invention is preferred to be processed into liquid, granular or powdery form and to be formed as an additive of food and drinks. In addition, it may be formed as a tablet, capsule, granule, or syrup so as to ingest separately from food and drinks.

Furthermore, when the excitement accelerating agent of the present invention is taken regularly for a long period of time, it can be used effectively as a nutritious tonic.

DESCRIPTION OF THE PREFERRED EMBODIMENT (Experiment 1)

In order to study the action of theanine in various doses with respect to the brain neurons, an experiment was conducted so as to measure the brain waves of rat after theanine was dosed thereto by adjusting the dose thereof to various amount.

1. Test specimen animal and group structure

After wister/st-type male rats whose age is 9 weeks (the weight is from 260 to 320 g) were kept for one week preliminarily, they were subjected to the electrode-imbedding surgery under anesthesia by NEMBUTAL to fix a thread electrode made of stainless steel in right and left forehead portions, and parallel-type dipolar electrodes made of stainless steel were imbedded in the hippocampus and the amygdala. During 4 days after the surgery, cefmetazone was applied by intramuscular injection for preventing the infection. After 10 days have passed since the surgery, three preliminary tests were conducted to form five groups from A Group to E Group, designating rats whose brain waves are stable as test specimens, and one group as 6 rats.

2. Preparation of the substance to be tested and dosage

A theanine balanced saline solution was prepared so as to be the following doses by dissolving theanine anhydride in the balanced saline solution, and dosed them to rats. In addition, theanine was dosed by the intravenous injection from the tail vein.

Theanine dose

A Group: Theanine dosed in 0 μmol/kg based on the weight

B Group: Theanine dosed in 1 μmol/kg based on the weight

C Group: Theanine dosed in 2 μmol/kg based on the weight

D Group: Theanine dosed in 5 μmol/kg based on the weight

E Group: Theanine dosed in 10 μmol/kg based on the weight

3. Measurement of the brain waves

Measurement of the brain waves was conducted by the dipolar-deriving method, and detected brain waves were passed through the high-pass filter having a cutoff frequency of 50 Hz and a damping characteristic of 24 db/oct, and were recorded on a photomagnetic disk at a sampling frequency of 200 Hz by a digital recorder (made by Tiac Co.: DR-M2a). Later, by using a personal computer (made by Nippon Denki Co.: PC-9801BA) and a waveform analysis software (made by Development Corporation: DADISP Work-sheet), the power spectrum was determined by the high-speed Fourier transform method with respect to the recorded brain waves to calculate the relative power of δ-wave, θ-wave, α1-wave, α2-wave and β-wave. The measurements of brain waves were conducted for three minutes, after 5 minutes, 15 minutes, 30 minutes and 60 minutes had passed, respectively, since the dose of theanine. And, smoothing of spectrum was conducted by adding a portion with little artifact 5 times, designating 5 seconds as one section.

In addition, generally, α-wave is the brain wave appearing while lying quietly with eyes closed, β-wave is the brain wave appearing when the brain is active lively, δ-wave is the brain wave appearing during a sound sleep, and θ-wave is the brain wave appearing while taking a nap.

4. Results of experiments

The relative powers of δ-wave, θ-wave, α1-wave, α2-wave and β-wave after 15 minutes, 30 minutes and 60 minutes have passed since the dose of theanine with respect to each portion of cortex, hippocampus and amygdala in each group described above are shown in FIGS. 1 to 9.

From these figures, it is found that in any of B Group (dose of 1 μmol/kg based on the weight), C Group (dose of 2 μmol/kg based on the weight), and D Group (dose of 5 μmol/kg based on the weight), the relative power of δ-wave appearing while sleeping is suppressed in any of cortex, hippocampus and amygdala, and the relative power of β-wave appearing while being active increases, and the increase rate thereof is conspicuous especially in C Group (dose of 2 μmol/kg based on the weight).

Furthermore, changes with lapse of time of the relative power with respect to each δ-wave, θ-wave, α1-wave, α2-wave and β-wave for every portion in B Group are shown in FIGS. 10–14, changes with lapse of time of the relative power with respect to each δ-wave, θ-wave, α1-wave, α2-wave and β-wave for every portion in C Group are shown in FIGS. 15–19, changes with lapse of time of the relative power with respect to each δ-wave, θ-wave, α1-wave, α2-wave and β-wave for every portion in D Group are shown in FIGS. 20–24, and changes with lapse of time of the relative power with respect to each δ-wave, θ-wave, α1-wave, α2-wave and β-wave for every portion in D Group are shown in FIGS. 25–29.

From these figures, it was found that the relative power of δ-wave appearing while sleeping was suppressed in any of cortex, hippocampus and amygdala in B Group (dose of 1 μmol/kg based on the weight) and C Group (dose of 2 μmol/kg based on the weight). On the contrary, in D Group (dose of 5 μmol/kg based on the weight) and E Group (dose of 10 μmol/kg based on the weight), the relative power of δ-wave was hardly suppressed.

Furthermore, in B Group (dose of 1 μmol/kg based on the weight) and C Group (dose of 2 μmol/kg based on the weight), the relative power of β-wave appearing while being active increased remarkably in the hippocampus and the amygdala, and the increase rate thereof was conspicuous especially in C group (dose of 2 μmol/kg based on the weight).

(Experiment 2)

In this experiment, in order to study the action of theanine with respect to the neural circuit when theanine prepared in various concentrations was dosed directly to the brain neurons, theanine was dosed in vitro to the primary cultured rat cerebral cortical neurons, and the period of the esthesic pigment preliminarily taken into neurons after dosing was observed comparatively.

1. Culture of the rat cerebral cortical neurons

A fetus was taken out from a rat being in 18 days of pregnancy, the brain of this fetus was cut open to cut out the cerebral cortical portion, and cut-out neurons of the cerebral cortical portion was isolated by the papain digestion anecsedia. On the other hand, a cover glass was put on a frame made of silicon resin, and the glass was coated with polyethylene imine. On this coating plate, said isolated neurons were uniformly scattered so as to become a predetermined concentration, and cultured while exchanging the culture solution for every few days. Thereby, the cultured neurons gradually formed the neural circuit, and exhibited a periodical excitement action spontaneously.

2. Preparation of the substance to be tested and dosage

First, using 6 kinds of cultured neurons cultured at the same time by the above-mentioned method, after exchanging of medium in each cultured well for neurons to isotonic buffer, fluorescent $Ca^{2+}$ esthesic pigment fura-2 was taken into neurons. Then, the luminous period (period of spontaneous excitement) of fura-2 inside of neurons was measured, and the average value of this measured value was designated as the control of each cultured neurons.

Then, theanine balanced saline solution prepared in various concentrations, that is, 10 μM, 50 μM, 100 μM, 400 μM, 700 μM, and 1000 μM was dosed in vitro to each cultured neuron, and the luminous period of fura-2 inside of each neuron was measured.

3. Measurement of fura-2 period

Figure 30:
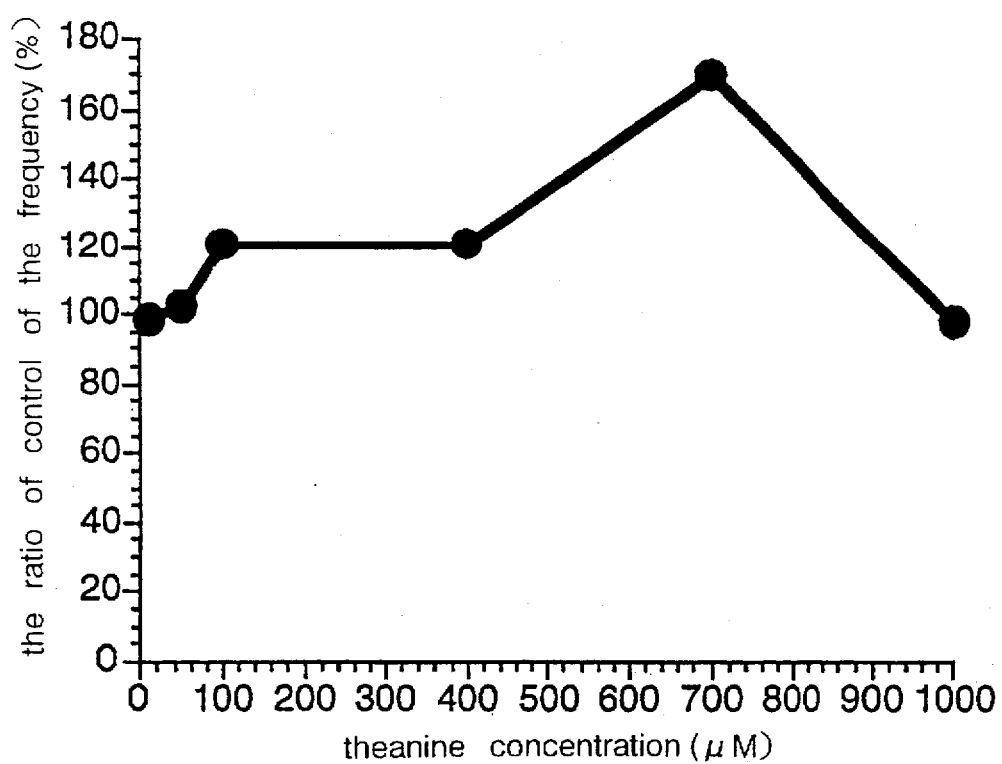
FIG. 30 is a view showing the excited state when theanine prepared in various concentrations is dosed in vitro to the brain neurons of a rat.

The luminous period of fura-2 inside of neurons was measured by the simultaneous multi-points observation apparatus (developed by Kudo et al. in 1986). The average value of the results of experiments repeated 5 times as described above is shown in FIG. 30. In this figure, the ratio of control of the frequency with respect to it is shown, by plotting theanine concentration (μM) on the abscissa and the reciprocal of the average period on the ordinate.

4. Results of experiments

From the above experiments, when theanine balanced saline solution was dosed in the concentration of 100 μM, 400 μM and 700 μM, excitability was observed, and in the case of 1000 μM, on the contrary, the tendency to suppress the excitement was observed.

Therefore, also in this experiment as in the above experiment 1, when the theanine content is adjusted to a very small amount less than a certain amount and dosed, it is observed that the excitement accerelating action of theanine is exerted.

What is claimed is:

1. A method for accelerating excitement comprising administering theanine to a mammal at a dose of about 0.17 to 2.8 mg/kg body weight.

2. The method of claim 1, wherein the theanine is administered as an aqueous solution.

3. The method of claim 1, wherein beta brain waves are activated.

4. The method of claim 1, wherein delta brain waves are inhibited.

5. The method of claim 1, wherein the theanine is administered in a form selected from the group consisting of liquids, granules, powders, food additives, drink additives, tablets, capsules and syrups.

6. The method of claim 5, wherein beta brain waves are activated.

7. The method of claim 5, wherein delta brain waves are inhibited.

* * * * *